(12) United States Patent
Jordan et al.

(10) Patent No.: US 12,059,456 B2
(45) Date of Patent: Aug. 13, 2024

(54) METHODS OF USING C1 ESTERASE INHIBITOR FOR IMPROVING EARLY ONSET AND LONG-TERM FUNCTION OF KIDNEY TRANSPLANTS FROM GRAFTS ASSOCIATED WITH DELAYED GRAFT FUNCTION

(71) Applicant: Cedars-Sinai Medical Center, Los Angeles, CA (US)

(72) Inventors: Stanley Jordan, Manhattan Beach, CA (US); Jua Choi, Porter Ranch, CA (US); Ashley Vo, Northridge, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 16/646,539

(22) PCT Filed: Sep. 14, 2018

(86) PCT No.: PCT/US2018/051045
§ 371 (c)(1),
(2) Date: Mar. 11, 2020

(87) PCT Pub. No.: WO2019/055763
PCT Pub. Date: Mar. 21, 2019

(65) Prior Publication Data
US 2020/0276283 A1    Sep. 3, 2020

Related U.S. Application Data

(60) Provisional application No. 62/559,312, filed on Sep. 15, 2017.

(51) Int. Cl.
*A61K 38/57* (2006.01)
*A61K 9/00* (2006.01)

(52) U.S. Cl.
CPC ............ *A61K 38/57* (2013.01); *A61K 9/0019* (2013.01)

(58) Field of Classification Search
CPC ...... A61K 38/57; A61K 9/0019; A61K 35/22; A61K 38/55; A61P 13/12; C07K 14/8121
See application file for complete search history.

(56) References Cited

U.S. PATENT DOCUMENTS

| | | |
|---|---|---|
| 2018/0104319 A1 | 4/2018 | Broom et al. |
| 2018/0133294 A1 | 5/2018 | Shapiro et al. |
| 2022/0265786 A1 | 8/2022 | Jordan et al. |

FOREIGN PATENT DOCUMENTS

| | | | |
|---|---|---|---|
| AU | 2018334213 A1 | 3/2020 | |
| CA | 3075686 A1 | 3/2019 | |
| EP | 1240904 A2 | 9/2002 | |
| JP | 2002322084 A | 11/2002 | |
| JP | 2016537380 A | 12/2016 | |
| JP | 2020-534280 A | 11/2020 | |
| JP | 2022543456 A | 10/2022 | |
| WO | 2015/077543 A1 | 5/2015 | |
| WO | WO-2015077543 A1 * | 5/2015 | ............. C07K 16/00 |
| WO | 2019/055763 A1 | 3/2019 | |
| WO | 2019185936 A2 | 10/2019 | |
| WO | 2021/026507 A1 | 2/2021 | |
| WO | 2022140435 A1 | 6/2022 | |

OTHER PUBLICATIONS

Jordan Assessing Safety and Efficacy of Preoperative and Post-Transplant C1 Inhibitor (Berinert®) vs. Placebo in Recipients of a Renal Allograft From Deceased High Risk Donors and Its Impact on DGF and IRI. FDA Archive History for NCT02134314 2014.*
PCT /US2014/066784 Application for published WO-2015077543, Uknis, including drawings. Nov. 21, 2014.*
Saidi et al., Challenges of Organ Shortage for Transplantation: Solutions and Opportunities. Int J Organ Transplant Med. 2014; 5(3): 87-96.*
Delpech et al, Inhibition of complement improves graft outcome ina pig model of kidney autotransplantation. J Transl Med. 2016; 14: 277.*
Montgomery et al, Plasma-Derived C1 Esterase Inhibitor for Acute Antibody-Mediated Rejection Following Kidney Transplantation: Results of a Randomized Double-Blind Placebo-Controlled Pilot Study. American Journal of Transplantation 2016; 16: 3468-3478.*
Rao et al, A Comprehensive Risk Quantification Score for Deceased Donor Kidneys: The Kidney Donor Risk Index. Transplantation vol. 88, No. 2, Jul. 27, 2009 p. 231-236.*
Stewart et al, New Insights Into the Alleged Kidney Donor Profile Index Labeling Effect on Kidney Utilization. American Journal of Transplantation 2017; 17: 2696-2704.*
OPTN A Guide to Calculating and Interpreting the Kidney Donor Profle Index (KDPI) Updated: Mar. 23, 2020. 11 pages.*
Berger et al., Potential Roles for C1 Inhibitor in Transplantation. Transplantation ▪ Jul. 2016 ▪ vol. 100 ▪ No. 7 p. 1415-1424.*
International Search Report and Written Opinion for PCT/US2018/051045 dated Dec. 12, 2018, 10 pages.
Berger et al., Potential Roles for C1 Inhibitor in Transplantation, Transplantation, 2016, vol. 100, pp. 1415-1424.
Dalle Lucca et al., Effects of C1 Inhibitor on Tissue Damage in a Porcine Model of Controlled Hemorrhage, Shock, 2012, vol. 38(1), pp. 82-91.
Danobeitia et al., Complement Inhibition Attenuates Acute Kidney Injury After Ischemia-Reperfusion and Limits Progression to Renal Fibrosis in Mice, PLOSOne, 2017, vol. 12(18), pp. 1-20.
Delpech et al., Inhibition of Complement Improves Graft Outcome in a Pig Model of Kidney Autotransplantation, J. Transl Med, 2016, vol. 14(277), pp. 1-13.
Huang et al., Three-Year Outcomes of a Randomized, Double-Blind, Placebo-Controlled Study Assessing Safety and Efficacy of C1 Esterase Inhibitor for Prevention of Delayed Graft Function in Deceased Donor Kidney Transplant Recepients, CJASN, 2020, vol. 15, pp. 1-9.

(Continued)

*Primary Examiner* — Delia M Ramirez
(74) *Attorney, Agent, or Firm* — Nixon Peabody LLP

(57) ABSTRACT

Described herein are methods for improving kidney function in subjects that have undergone kidney transplant. An effective amount of one or more complement component 1 esterase inhibitors is administered to the subject, resulting in long-term improvement on kidney allograft function.

7 Claims, 12 Drawing Sheets

(56) References Cited

OTHER PUBLICATIONS

Jordan et al., A Phase I/II, Double-Blind, Placebo-Controlled Study Assessing Safety and Efficacy of C1 Esterase Inhibitor for Prevention of Delayed Graft Function in Deceased Donor Kidney Transplant Recipients, Am J. Transplant, 2018, vol. 18, pp. 2955-2964.
Kumar et al., Cellular and Molecular Pathways of Renal Repair after Acute Kidney Injury, Kidney International, 2018, vol. 93, pp. 27-40.
Lim et al., Association Between Delayed Graft Function and Graft Loss in Donation after Cardiac Death Kidney Transplants—A Paired Kidney Registry Analysis, Transplantation, 2017, vol. 101(6), pp. 1139-1143.
Lim et al., Medical Therapies to Reduce Delayed Graft Function and Improve Long-Term Graft Survival, CJASN, 2020, vol. 15, pp. 1-3.
Liu et al., Molecular Characterization of the Transition from Acute to Chronic Kidney Injury Following Ischemia/Reperfusion, JCI Insight, 2017, vol. 2(18), pp. 1-18.
Montgomery et al., Plasma-Derived C1 Esterase Inhibitor for Acute Antibody-Mediated Rejection Following Kidney Transplantation: Results of a Randomized Double-Blind Placebo-Controlled Pilot Study, American Journal of Transplantation, 2016, vol. 16, pp. 3468-3478.
Vo et al., A Phase I/II Placebo-Controlled Trial of C1-Inhibitor for Prevention of Antibody-Mediated Rejection in HLA Sensitized Patients, Transplantation, 2015, vol. 99(2), pp. 299-308.
Walport et al., Complement First of Two Parts, Advances of Immunology, N Eng J Med, 2001, vol. 344(14), pp. 1058-1066.
Walport et al., Complement Second of Two Parts, Complement at the Interface Between Innate and Adaptive Immunity, Advances of Immunology, N Eng J Med, 2001, vol. 344(15), pp. 1140-1144.
U.S. Department of Health and Human Services Food and Drug Administration Center for Drug Evaluation and Research (CDER), Delayed Function in Kidney Transplantation: Developing Drugs for Preventative Guidance for Industry, 2017, pp. 1-15.
Clinicaltrials.gov, C1INH Inhibitor Preoperative and Post Kidney Transplant to Prevent DGF and IRI (C1INHDGF), Study NCT02134314 on May 8, 2014, pp. 2-9, retrieved from [https://clinicaltrials.gov/ct2/history/NCT02134314 ?V_1 =View#StudyPageTop].
International Preliminary Report on Patentability for PCT/US2018/051045 dated Dec. 12, 2018, 7 pages.
International Search Report and Written Opinion for PCT/US2020/45507 dated Aug. 7, 2020, 8 pages.
EP 18857228.3 Extended Search Report dated Apr. 20, 2021, 16 pages.
Castellano et al., Therapeutic targeting of classical and lectin pathways of complement protects from ischemia-reperfusion-induced renal damage. Am J Pathol, 2010, vol. 176, pp. 1648-1659.
Clinicaltrials.gov, Safety & Tolerability of Berinert (CI Inhibitor) Therapy to Prevent Rejection—Full Text View—ClinicalTrials.gov11 , XP055758792, Retrieved from: https://clinicaltrials.gov/ct2/show/NC T01134510, Mar. 21, 2017.
Clinicaltrials.gov, History of Changes for Study: NCT02435732, XP055758820, Retrieved from: https://clinicaltrials.gov/ct2/history/NCT02435732?V 3=View#StudyPageTop, Mar. 30, 2017.
Clinicaltrials.gov, History of Changes for Study: NCT02134314, XP055758302, Retrieved from: https://clinicaltrials.gov/ct2/history/NCT02134314?V 5=View#StudyPageTop, Jul. 27, 2017, Version 5.
Clinicaltrials.gov, RUCONEST® as a Therapeutic Strategy to Reduce the Incidence of Delayed Graft Function, Retrieved from: https://clinicaltrials.gov/ct2/show/NCT03791476 on Jan. 2, 2019.
Danobeitia et al., Targeted Donor Complement Blockade After Brain-Death Prevents Delayed Graft Function in a Non-Human Primate Model of Kidney Transplantation, American Journal of Transplantation, 2020, vol. 20(6), pp. 1513-1526.
Delpech et al., Inhibition of complement improves graft outcome in a pig model of kidney autotransplantation, J Transl Med, 2016, vol. 14, p. 277.
Jordan et al., Imlifidase Desensitization in Crossmatch-positive, Highly Sensitized Kidney Transplant Recipients: Results of an International Phase 2 Trial (Highdes), Transplatation, 2021, vol. 105(8), pp. 1808-1817.
Berger et al., Update on C1 Esterase Inhibitor in Human Solid Organ Transplantation, Transplantation, 2019, vol. 103(9), pp. 1763-1775.
EPO Exam Report for EP 18857228.3 dated Mar. 31, 2022.
International Search Report and Written Opinion for PCT/US2021/64678, 9 pages.
Clinicaltrials.gov, Berinert (C1INH) vs Placebo for DGF/IRI, Study NCT04696146 first posted on Jan. 6, 2021.
Ammerman et al., Abstract #228, Assessing the Safety & Efficacy of Renal Artery Infusions of C1 Esterase Inhibitor (c1inh) in Kidney Transplant Recipients at Risk for Iri/Dgf, American Transplant Congress 2023, 2023, vol. 23(6), Supplement 1.
Jordan et al., C1 Esterase Inhibitor (C1INH) Treatment at Kidney Transplant Improves Long-Term Outcomes in Patients at Risk for Ischemia/Reperfusion Injury & Delayed Graft Function, Meeting Abstracts (Abstract No. D256) of 2019 American Transplant Congress, Poster Session, Jun. 4, 2019.
Supplementary European Search Report for EP 20849668 dated Jun. 29, 2023.

* cited by examiner

C1INH vs. Placebo Schema

METHODS OF USING C1 ESTERASE INHIBITOR FOR IMPROVING EARLY ONSET AND LONG-TERM FUNCTION OF KIDNEY TRANSPLANTS FROM GRAFTS ASSOCIATED WITH DELAYED GRAFT FUNCTION

CROSS-REFERENCE TO RELATED APPLICATIONS

This application is a National Phase of International Application No. PCT/US2018/051045 filed Sep. 14, 2018, which designated the U.S. and that International Application was published under PCT Article 21(2) in English, which also includes a claim of priority under 35 U.S.C. § 119(e) to U.S. Provisional Application No. 62/559,312, filed on Sep. 15, 2017, the entirety of which is hereby incorporated by reference.

FIELD OF THE INVENTION

The invention relates to improving organ function in subjects that have undergone organ transplant.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Studies on renal transplantation outcomes have traditionally focused on patient and graft survival with little consideration of graft function. Although graft loss is the worst outcome, grafts with impaired function require the most intense follow-up, are economically costly and require rigorous clinical management to preserve functional integrity. This has become a larger concern since implementation of United Network for Organ Sharing (UNOS) policies which allocate higher risk kidneys to older recipients. This is likely to increase the risk for delayed graft function (DGF) and poorer allograft function. Details can be seen in the website of the Organ Procurement and Transplantation Network by the U.S. Department of Health & Human Services.

Data recently reported by Taber et al. analyzed the impact of the new kidney allocation system (KAS) on perioperative outcomes and cost in kidney transplantation. The authors analyzed 38,016 kidney transplant procedures performed over a 3.8-year period. They conclude that the KAS resulted in a significant increase in DGF rates (from 5.4% to 7.4%) as well as increased in total hospital costs and readmission rates. Stewart et al. examined the changes in deceased donor transplantation one year after implementation of the new KAS. These authors concluded that despite increasing the fairness of organ allocation, the system has increased the cost of transplantation, increased cold ischemia times and DGF rates.

DGF is a term used to describe the lack of acceptable function of a kidney after transplantation that is likely due to ischemia-reperfusion injury (IRI). DGF is associated with inferior function in kidney transplants at 1 and 2 years post-transplant. In the presence of DGF, kidneys are more likely to have adverse outcomes including decreased functional graft survival, patient survival, and increased acute rejection. Kidneys from extended criteria deceased donors (ECD), now referred to as high Kidney Disease Profile Index (KDPI), are also associated with higher rates of DGF and poorer long-term survival. In an analysis of outcomes from 9,134 recipients of donor after cardiac death (DCD) and brain-death donor kidneys, donor age ≥60 years was identified as a risk factor for graft failure and reduced long-term renal function. These investigators found that recipients of ECD kidneys have twice the risk of graft failure compared to recipients of younger donor kidneys.

Historically DGF has been defined as the requirement for dialysis during the first week post-transplantation, however this is not standardized and the decision to dialyze varies from center to center. Efforts have been made to scientifically quantify DGF in a more stringent manner with various alternative definitions of DGF including measurement of time to eGFR of 10 mL/min. The U.S. Food and Drug Administration (FDA) recently released guidelines for defining relevant end points for studies of new therapies for the prevention of IRI/DGF. The FDA guidelines highlight the need for relevant therapeutic studies in IRI/DGF since no therapy, to date, has demonstrated efficacy. In addition, a description of relevant surrogate end points, including assessment of the need for dialysis at 30 days and allograft function at one year, is recommended.

Recently, Lim et al. described a more relevant assessment of the impact of DGF in recipients of kidney transplants from donors after cardiac death (DCD). These investigators analyzed data from 74 pairs of DCD transplants. The authors conclude that recipients of DCD kidneys who experience DGF have a higher incidence of overall graft loss. Thus, strategies to reduce the risk for DGF could improve graft survival in DCD kidney transplants.

SUMMARY

The following embodiments and aspects thereof are described and illustrated in conjunction with systems, compositions and methods which are meant to be exemplary and illustrative, not limiting in scope.

Methods for improving long-term graft function, or reducing the likelihood of or treating delayed graft function in a subject, are provided. Various embodiments provide the subject has undergone kidney transplant, and/or has received or will receive kidney from extended criteria deceased donors, e.g., a donor over the age of 60, a donor over the age of 50 with two of the following: a history of high blood pressure, a creatinine (blood test that shows kidney function) greater than or equal to 1.5, or death resulting from a stroke.

Various embodiments provide administering to the subject an effective amount of one or more C1 esterase inhibitors, which results in improved graft kidney function or reduction in the delayed kidney graft function, especially in months or about one-year post-transplantation. C1 esterase inhibitor, or C1-inhibitor, is a protease inhibitor belonging to the serpin superfamily. It inhibits the complement system to prevent spontaneous activation. Naturally occurring C1-inhibitor is an acute-phase protein that circulates in blood. C1-inhibitor irreversibly binds to and inactivates C1r and C1s proteases in the C1 complex of classical pathway of complement. MASP-1 and MASP-2 proteases in MBL complexes of the lectin pathway are also inactivated. C1-inhibitor also inhibits proteases of the fibrinolytic, clotting, and kinin pathways. Exemplary C1 esterase inhibitors for use in the methods include a purified C1 esterase inhibitor from human blood (CINRYZE®), a recombinant analogue of human complement component 1 esterase inhibitor (RU-CONEST®), a recombinant human (rh) C1 esterase inhibitor produced in the milk of transgenic rabbits (RHUCIN®), and a human plasma-derived, purified, pasteurized, lyophilized concentrate of C1 esterase inhibitor (BERINERT®).

In some embodiments, the methods are characterized by improved kidney graft function in the long term (3, 4, 5, 6, 7, 8, 9, 10, 11 or 12 months post-transplantation) compared to kidney function within one week following transplantation of the subject or to a control subject having undergone a kidney transplant and experiencing delayed graft function who has not had a therapeutically effective amount of one or more C1 esterase inhibitors.

In one embodiment, C1 esterase inhibitor (C1INH) and placebo were administered to patients receiving kidney transplant from deceased high risk donors. C1 esterase inhibitor, at 50 units/kg and placebo were given in two doses, on the day of transplant and 24 hours after operation. No significant difference in delayed graft function (DGF), defined as dialysis requirement within first week post-transplantation, was observed. However, C1 esterase inhibitor treatment group showed significant reduction in dialysis requirement between the second and fourth week post-transplantation. In addition, C1 esterase inhibitor treatment group showed significantly improved estimated glomerular filtration rates (eGFR), a kidney function measurement, one year post-operation, and the values were comparable to healthy individuals. These results suggest that treatment with C1 esterase inhibitor or other C1 esterase inhibitors can significantly improve long-term kidney function.

The study showed a positive benefit in reducing the number of patients needing dialysis two to four weeks post-transplant. This rapid recovery was also associated with significantly better renal function at one year post-transplant. Therefore, provided herein are methods for improving long-term kidney graft function in a subject that has undergone a kidney transplant. The instant invention, developed in robust controlled trial, shows that C1INH works to reduce the rate of dialysis at 2-4 weeks and improved graft function at one year post-transplant. To date, no other drug has shown this degree of benefit.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
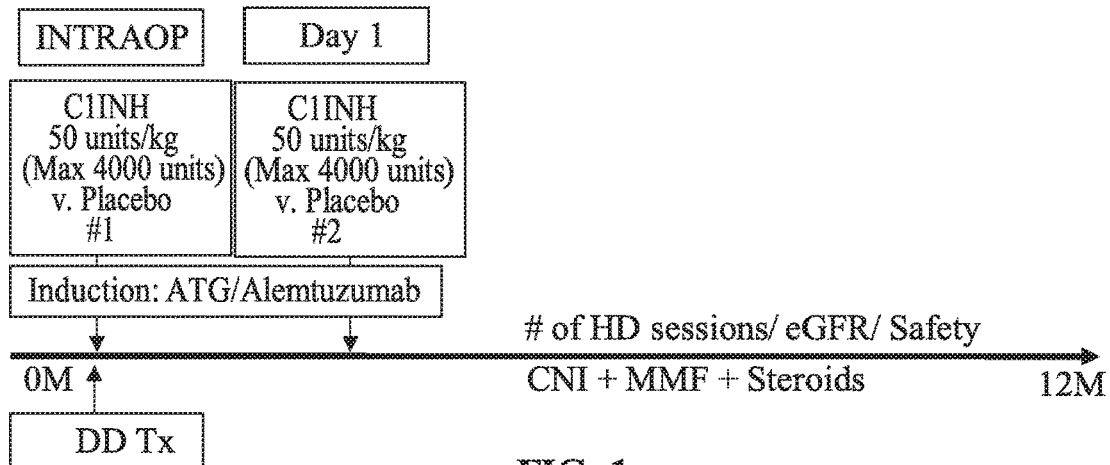
FIG. 1 is a diagram depicting the protocol used in the Example. Briefly, patients eligible for the study were randomized to receive C1INH (50 Units/kg) v. placebo intraoperatively and on day 1 post-transplant. Induction therapy was alemtuzumab 30 mg subcutaneous for patients receiving HLA incompatible kidneys and thymoglobulin 1.5 mg daily×4 days for non-HLA sensitized deceased donor recipients. All patients were maintained on tacrolimus, mycophenolate mofetil and steroids per center protocol. The need for dialysis and analysis of glomerular filtration rates were performed up to 1 year post-transplant. All patients had pre-implantation biopsies to determine extent of pre-existing donor injury.
Figure 2:
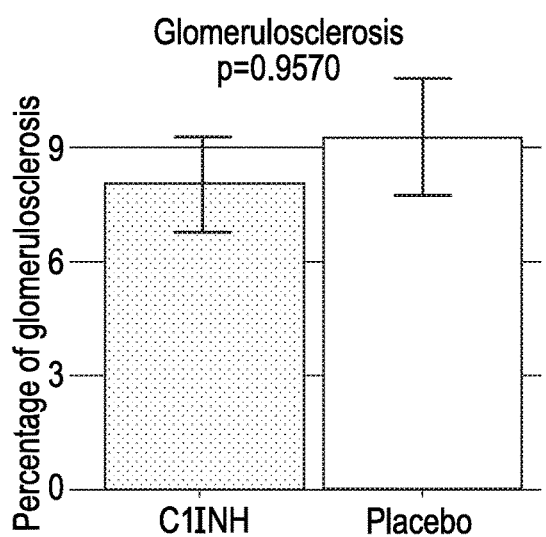
FIGS. 2-5 are bar graphs showing kidney allograft pre-implantation biopsy phenotypes, according to the treatment (C1INH vs. Placebo). Here, we examined the extent of pre-existing glomerulosclerosis (FIG. 2), arteriosclerosis (FIG. 4), atrophy-fibrosis (FIG. 3) and arteriolar hyalinosis (FIG. 5) in renal allografts implanted in the C1INH and placebo group. Briefly, no significant differences in any parameters were seen. The T bars indicate standard errors. Abbreviations: C1INH: C1 esterase inhibitor.
Figure 3:
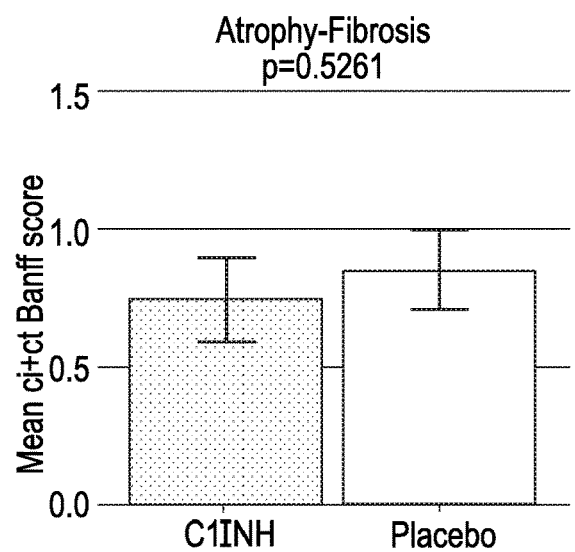
Figure 4:
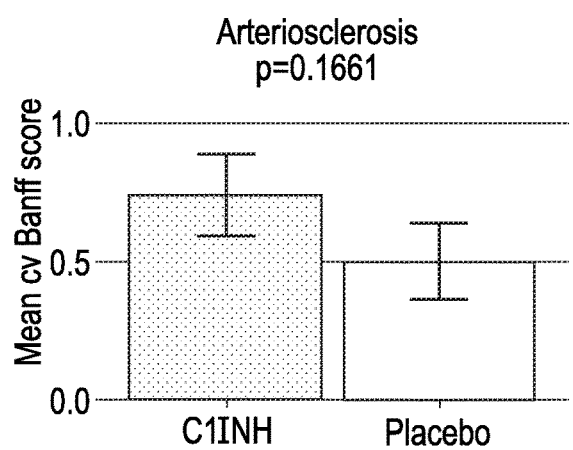
Figure 5:
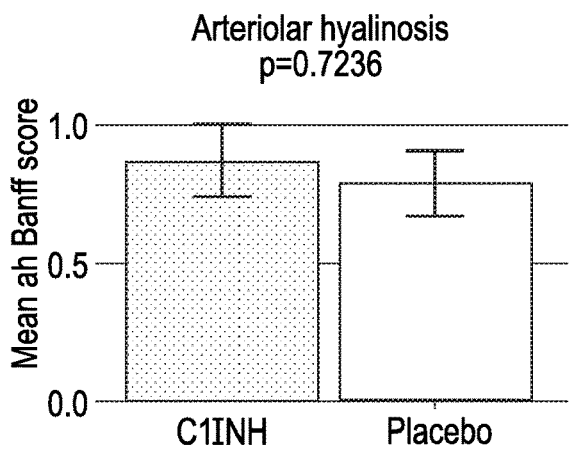

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, NY 2006); Smith, *March's Advanced Organic Chemistry Reactions, Mechanisms and Structure* 7$^{th}$ ed., J. Wiley & Sons (New York, NY 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of kidney allograft function, delay or slowing of renal function, and amelioration or palliation of symptoms associated with end stage renal disease.

The terms "C1-Inhibitor," "C1 esterase Inhibitor," "C1-INH" and "C1INH" refer to the proteins or fragments thereof that function as serine protease inhibitors to inhibit proteases associated with the complement system, preferably proteases C1r and C1s as well as MASP-1 and MASP-2, with the kallikrein-kinin system, preferably plasma kallikrein and factor XIIa, and with the coagulation system, preferably factor XIa. In addition, C1-INH can serve as an anti-inflammatory molecule that reduces the selectins-mediated leukocyte adhesion to endothelial cells. C1-INH as used herein can be a native serine protease inhibitor or active fragment thereof, or it can comprise a recombinant peptide, a synthetic peptide, peptide mimetic, or peptide fragment that provides similar functional properties—e.g., the inhibition of proteases C1r and C1s, and/or MASP-1 and MASP-2 and/or factor XIIa and/or factor XIa. For further disclosure regarding the structure and function of C1-Inhibitor, see U.S. Pat. Nos. 4,915,945; 5,939,389; 6,248,365; 7,053,176; and WO 2007/073186.

In some embodiments, the inhibitor is a plasma-derived or a recombinant C1-Inhibitor. In a further preferred embodiment said inhibitor is identical with the naturally occurring human protein or a variant thereof. The C1-INH shall encompass all natural occurring alleles which have the same function as the C1-inhibitor. In one embodiment said inhibitor is the human C1 Esterase Inhibitor.

In another embodiment the C1-inhibitor according to the present invention is modified to improve bioavailability and/or half-life, to improve efficacy and/or to reduce potential side effects. The modification can be realized by recombinant or other steps. Examples for such a modification could be a glycosylation or an albumin fusion of the described C1-inhibitor. For further disclosure regarding the glycosylation and the albumin fusion of proteins see WO 01/79271.

In various embodiments, C1-Inhibitor can be produced according to methods known to one of skill in the art. For example, plasma-derived C1-INH can be prepared by collecting blood plasma from several donors. Donors of plasma should be healthy as defined in the art. Preferably, the plasma of several (1000 or more) healthy donors is pooled and optionally further processed. An exemplary process for preparing C1-inhibitor for therapeutic purposes is disclosed in U.S. Pat. No. 4,915,945, the disclosure of which is hereby incorporated in its entirety. Alternatively, in some embodiments C1-INH can be collected and concentrated from natural tissue sources using techniques known in the art. Commercially available products comprising C1-inhibitor are, e.g. plasma-derived CINRYZE® (Viropharma), recombinant RUCONEST® or RHUCIN® (both Pharming), and plasma-derived BERINERT® (CSL Behring). BERINERT® is indicated for treatment of hereditary angioedema and congenital deficiencies. Recombinant C1-INH can be prepared by known methods.

As used herein, the term "administering," refers to the placement of an agent or a composition as disclosed herein into a subject by a method or route which results in at least partial localization of the agents or composition at a desired site. "Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In an embodiment, the subject is human. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., kidney failure) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering C1 esterase inhibitor. Measured or measurable parameters include clinically detectable markers of disease, for example, elevated or depressed levels of a biological marker, as well as parameters related to a clinically accepted scale of symptoms or markers for fibrosis and/or inflammation. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

C1 esterase inhibitor is a unique serine protease inhibitor that blocks activation of the human complement system through two distinct pathways. First, C1 esterase inhibitor blocks the assemblage of the C1q-r-s complex (classical pathway) that is critical for conversion of nascent C3 to C3a and C3b which then activate C5b to C9 to form the membrane attack complex. Second, C1 esterase inhibitor inhibits complement activation through the mannose-binding lectin (MBL)/MBL-serine protease pathway, usually activated by bacterial pathogens. C1 esterase inhibitor inhibition of complement activation is proximal and may be of particular value in blocking multiple downstream activation pathways. The MBL/MBLSP is important in mediating ischemic reperfusion injury (IRI) especially in kidneys. The inventors evaluated C1 esterase inhibitor in a placebo controlled double-blinded trial to determine the potential benefits of C1 esterase inhibitor treatment prior to kidney transplant in prevention of IRI and delayed graft function (DGF).

In one embodiment, C1 esterase inhibitor and placebo were administrated to patients receiving kidney transplant from deceased high risk donors. C1 esterase inhibitor at 50 Units/kg and placebo were given in two doses on the day of transplantation and 24 hours after operation. Although no significant difference in delayed graft function (DGF) defined as dialysis requirement, was observed within $1^{st}$ week post-transplantation; C1 esterase inhibitor treatment group showed significant reduction in dialysis requirement between $2^{nd}$ and $4^{th}$ week post-transplantation. In addition, C1 esterase inhibitor treatment group showed significantly improved estimated glomerular filtration rates (eGFR), a kidney function measurement, one year post-operation, and the values were comparable to healthy individuals. The C1 esterase inhibitor treatment method can significantly improve long-term kidney function.

Accordingly, provided herein are methods for improving graft organ function in a subject that has undergone a solid organ transplant. The method includes administering to the subject a therapeutically effective amount of one or more C1 esterase inhibitors. In an embodiment, the method includes treating the organ to be transplanted with an effective amount of C1 esterase inhibitor before implantation. In an exemplary embodiment, the C esterase inhibitor includes commercially available products comprising C1-inhibitor, e.g. plasma-derived CINRYZE® (Viropharma), recombinant RUCONEST® or RHUCIN® (both Pharming), and plasma-derived BERINERT®. In one embodiment, the organ is a kidney. In some embodiments, the solid organ transplant is kidney, heart, liver, lung, small bowel, pancreas and bone marrow transplantation.

Further provided herein are methods for improving graft kidney function in a subject that has undergone kidney transplant and is at a risk of having DGF and/or IRI. The method includes administering to the subject a therapeutically effective amount of one or more C1 esterase inhibitors. In an embodiment, the method includes treating the kidney to be transplanted with an effective amount of C1 esterase inhibitor before implantation of the kidney. In an exemplary embodiment, the C1 esterase inhibitor includes commercially available products comprising C1-inhibitor, e.g. plasma-derived CINRYZE® (Viropharma), recombinant RUCONEST® or RHUCIN® (both Pharming), and plasma-derived BERINERT®.

Also provided herein are methods for improving graft kidney function in a subject that has undergone kidney transplant. The method includes administering to the subject a therapeutically effective amount of one or more C1 esterase inhibitors. In an embodiment, the method includes treating the kidney to be transplanted with an effective amount of C1 esterase inhibitor before implantation of the kidney. In an exemplary embodiment, the C1 esterase inhibitor includes commercially available products comprising C1-inhibitor, e.g. plasma-derived CINRYZE® (Viropharma), recombinant RUCONEST® or RHUCIN® (both Pharming), and plasma-derived BERINERT®.).

In some embodiments, the therapeutically effective amount of C1 esterase inhibitor is about 25-50 units/kg, about 50-75 units/kg, about 75-100 units/kg or about 50 units/kg.

In some embodiments, the therapeutically effective amount of C1 esterase inhibitor is administered on the day of the transplant. In some embodiments, the therapeutically effective amount C1 esterase inhibitor is administered to the subject about 24 hours after transplant. In some embodiments, the therapeutically effective amount C1 esterase inhibitor is administered to the subject on the day of the transplant and about 24 hours after transplant.

Some embodiments provide the organ (e.g., kidney) is from extended criteria deceased donors, e.g., a donor over the age of 60, a donor over the age of 50 with two of the following: a history of high blood pressure, a creatinine (blood test that shows kidney function) greater than or equal to 1.5, or death resulting from a stroke.

In some embodiments of the methods described herein, the organ is treated with C1 esterase inhibitors prior to implantation of the organ in the subject. In some embodiments, the organ is treated with an effective amount of C1 esterase inhibitors at the time of procurement of the organ from the donor. In some embodiments, the organ is treated with an effective amount of C1 esterase inhibitors about 36-30 hours, about 30-25 hours, about 25-20 hours, about 20-15 hours, about 15-10 hours, about 10-5 hours, about 5-1 hour or combinations thereof, prior to implantation of the organ in the subject. In some embodiments, the organ is treated with an effective amount of C1 esterase inhibitors about 1 hour, 2 hours, 3 hours, 4 hours, 5 hours, 6 hours, 7 hours, 8 hours, 9 hours, 10 hours, 10-15 hours, 15-20 hours, 20-24 hours or combinations thereof, prior to implantation of the organ in the subject.

In some embodiments, the C1 esterase inhibitor is administered to the subject intravenously.

In some embodiments, delayed graft function (DGF) is observed in the subject that has undergone kidney transplant. DGF comprises need for dialysis in the subject within seven days of transplant. In various embodiments reduction in dialysis requirement is observed about 2 weeks, 3 weeks or 4 weeks after the transplant. In further embodiments, the reduction in dialysis requirement is observed about 2-4 weeks, 1-3 months, 3-6 months, 6-9 months, 9-12 months or 12-15 months after the transplant.

In various embodiments, kidney function in the subject that has undergone kidney transplant is improved in the long-term, for example about 3-6 months, 6-9 months, 9-12 months, 12-15 months or more than 15 months after transplant. In various embodiments, improved kidney function includes increased estimated glomerular filtration rates, decreased serum creatinine levels, increased creatinine clearance, and/or increased urine output.

In some embodiments, in subjects that have undergone kidney transplant, the levels of the HLA antibodies, serum creatinine levels and/or estimated glomerular filtration rates (eGFR) is increased by at least about 10%, 20%, 30%, 40%, 50%, 60%, 70%, 80% 90% or 100% or combinations thereof. In some embodiments, in subjects that have undergone kidney transplant, the levels of the HLA antibodies, serum creatinine levels and/or eGFR is increased by at least about 1-fold, 2-fold, 3-fold, 4-fold, 5-fold, 6-fold, 7-fold, 8-fold, 9-fold, 10-fold, 15-fold, 20-fold, 30-fold, 50-fold, 15-fold, 100-fold or combinations thereof.

In some embodiments of the invention, the therapeutically effective amounts of one or more C1 esterase inhibitors can be in the range of about 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day.

In further embodiments of the invention, the therapeutically effective amounts of one or more C1 esterase inhibitors for use with the methods described herein may be in the range of 1-5 units/kg, 5-10 units/kg, 10-50 units/kg, 50-100 units/kg, 100-150 units/kg, 150-200 units/kg, 100-200 units/kg, 200-300 units/kg, 300-400 units/kg, or 400-500 units/kg.

In various embodiments, the therapeutically effective amounts of one or more C1 esterase inhibitors for use with the methods described herein may be administered at any one or more of the dosages described herein at least once 1-7 times per week, 1-7 times per month, 5-10 times per month or combinations thereof for 1 month, 2 months, 3 months, 4 months, 5 months 6 months, 7 months, 8 months, 9 months, 10 months, 11 months, 12 months, 14 months, 16 months, 18 months, 20 months, 22 months, 24 months or combinations thereof.

Typical dosages of an effective amount of one or more C1 esterase inhibitors can be in the ranges recommended by the manufacturer where known therapeutic compounds are used, and also as indicated to the skilled artisan by the in vitro responses or responses in animal models. For example, complement C1 esterase inhibitor (BERINERT®) is currently recommended at 50 Units/kg (rounded to the nearest 500 Units) intravenously. The same or similar dosing can be used in accordance with various embodiments of the present invention, or an alternate dosage may be used in connection with alternate embodiments of the invention. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

In various embodiments, the effective amounts of one or more C1 esterase inhibitors is administered during organ transplants and up to any one or more of one month, two months, six months, twelve months, 18 months, 24 months or 30 months after transplant.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1

In Example 1, C1INH refers to BERINERT®. Delayed graft function (DGF) in kidney allograft recipients is traditionally defined as need for dialysis during the first week after transplantation. DGF is related to ischemia reperfusion injury (IRI) that impacts long-term allograft function and survival. There are no approved therapies for prevention of IRI/DGF. Complement activation induced by IRI may induce DGF. Here we investigate the ability of the complement inhibitor, C1INH to prevent IRI/DGF in kidney transplant recipients.

70 patients receiving cadaveric kidney transplants at risk for DGF were randomized to receive C1INH 50 U/kg (#35) or placebo (#35) intraoperatively and 24 hours later. The primary end point was need for hemodialysis during the first week post-transplant. Assessments of renal function (one year) and dialysis dependency (one month) were accomplished. Complications and safety of therapy was also recorded. Patients were followed for 1 year.

Patients randomized to C1INH and placebo exhibited similar characteristics with no significant differences in cold-ischemia time or other risk factors for DGF. C1INH did not result in reduced number of dialysis sessions at 1 week post-transplant, but significantly fewer patients (p=0.0232) required dialysis 2-4 weeks post-transplant. Patients at highest risk for DGF (KDPI >85) benefited most from C1INH therapy. Significantly better renal function was seen at one year in C1INH treated patients (p=0.04). No significant adverse events were noted in the C1INH group.

Although the primary end point was not met, significant reductions in the need for dialysis two weeks post-transplant and improvements in long-term allograft function were seen with C1INH treatment.

Example 2

In Example 2, C1INH refers to BERINERT®.

Complement as a Mediator of Ischemia Reperfusion Injury (IRI)

Complement is a system of proteins considered part of the innate immune system known to be activated by damage-associated molecular patterns (DAMPs) induced by ischemia. IRI also stimulates local C3 production in renal tubular cells, which can amplify local activation. Complement activation by the lectin and/or classical pathways may deposit C3 fragments on ischemic tissues, which promote leukocyte adherence, generate potent chemo-attractants such as C5a, and form the C5b-C9 Membrane Attack Complex (MAC), which induces cell death and cytokine release. Thus, inhibition of complement activation might have potential benefit in prevention of IRI/DGF.

Complement exists in two distinct compartments (central and local). The central compartment is produced in the liver and is responsible for all circulating complement factors. The peripheral compartment included complement generated locally in organs such as the CNS and kidneys. Activation of complement in the peripheral compartments appears to be regulated primarily by IRI. Briefly, IRI stimulates C3 production in the renal tubular cells that is subsequently cleaved by the manose binding lectin/manose associated serine protease (MBL/MASP) or alternative pathway. C3b generated then activates C5 to C5a and C5b. C5b forms the C5b-C9 Membrane Attack Complex (MAC) which induces cell death and cytokine release. Thus, inhibition of complement activation might have potential benefit in prevention of IRI/DGF.

Evidence for Use of C1INH to Prevent IRI and DGF

C1 esterase inhibitor (C1INH) is a multifunctional protease inhibitor encoded by the SERPING1 gene and a member of the serpin superfamily. C1INH inhibits multiple enzymes, including C1s and C1r in the classic pathway of complement; and mannan-binding lectin-associated serine proteases (MASP-1 and MASP-2) in the lectin complement pathway. C1INH is heavily glycosylated and can directly inhibit leukocyte adherence by blocking selectin binding. C1INH is approved to treatment of hereditary angioedema.

Several experimental models of IRI have shown improvement in functional and pathological characteristics after treatment with C1INH. Based on these observations, we hypothesize that the use of C1INH in patients receiving deceased donor kidney transplants with high risk for IRI-induced DGF might be beneficial in reducing DGF and improving outcomes post-transplant. C1INH may have advantages since it inhibits the classic and MBL/MASP pathways known to be important in complement-mediated IRI. Here we present the results of a double blinded, phase I/II controlled trial of C1INH v. placebo for prevention of DGF in deceased donor kidney transplants.

Patients & Methods

We conducted a Phase I/II double blinded placebo controlled trial investigating the safety and efficacy of C1INH to reduce DGF after high-risk deceased donor kidney transplantation. Studies were performed entirely at Cedars-Sinai Medical Center, Los Angeles, CA Protocols were approved by IRB and all patients provided written, informed consent.

Eligible patients were 18 to 70 years with end-stage renal disease (ESRD) on dialysis, awaiting deceased donor kidney transplantation on the United Network for Organ Sharing (UNOS) waitlist. Other eligibility criteria included risks for DGF based on the following: Recipients of kidney allograft from ECD (or KDPI score >85) donors, recipients of kidney allograft from DCD donors and recipients of kidney allograft other than ECD and DCD who have risk index of 3 to 8 (minimum 3 and maximum 8) for DGF, based on the criteria in the risk index detailed in Table 1. A consensus definition of DGF is the requirement for dialysis during the first week post-transplant. Here, we used a modified definition of DGF, excluding all dialysis sessions performed in the first 24 hours post-transplant for hyperkalemia or volume overload.

At transplantation, induction therapy consisted of alemtuzumab 30 mg subcutaneous once immediately post-operatively (for highly sensitized patients) or rabbit antithymocyte globulin 1.5 mg/kg per day given daily for 4 days postoperatively for nonsensitized patients. All patients were maintained on tacrolimus or cyclosporine, mycophenolate mofetil, and corticosteroids post-transplant per center protocol. Local institution treatment guidelines were utilized for prophylaxis against viral, bacterial, and fungal infections. All patients received meningococcal vaccination before transplantation and received prophylactic antibiotics for 1 month post-transplant to prevent and decrease risk of *Neisseria meningitidis* infection.

TABLE 1

| Risk Factors for Delayed Graft Function | |
|---|---|
| Characteristic | Risk Index* |
| Donor Age (years) | |
| <40 | 0 |
| 41-49 | 1 |
| 50-54 | 2 |
| 55-59 | 3 |
| >60 | 6 |
| Cold Ischemia Time (hours) | |
| 0-12 | 0 |
| 13-18 | 1 |
| 19-24 | 2 |
| 24-30 | 3 |
| 31-36 | 4 |
| >37 | 6 |
| Recipient Race | |
| Non-Black | 0 |
| Black | 1 |
| Recipient with Diabetes | |
| Has Diabetes | 1 |
| No Diabetes | 0 |
| Donor cause of death due to CVA | |
| Donor age <50 years | 0 |
| Donor age >50 years | 3 |
| Donor with Terminal Cr | |
| TCr > 4 | 3 |
| TCr ≥ 2-4 | 2 |
| TCr < 2 | 0 |

Clinical Assessments

Assessments included routine laboratory tests, pre-transplant biopsy, vital signs and collection of data related to adverse events (AE) and serious adverse events (SAE). All AEs and SAEs were recorded, graded, and reported to the Institutional Review Boards (IRB) at all centers, the study sponsor, and regulatory authorities. Samples for analysis of C1INH levels, complement levels, as well as coagulation factors were collected as per protocol. After transplantation, we assessed the need for hemodialysis, excluding dialysis sessions performed within the first 24 hours for hyperkalemia or volume overload, for up to one month post-transplant. In addition, estimated glomerular filtration rates (eGFRs) using the MDRD equation were performed on each patient up to 1 year post-transplant. Patient and graft survival were also noted.

Study Oversight

The study was approved by the IRB at Cedars-Sinai Medical Center (IRB #37068) and was conducted in accordance with the Declaration of Helsinki, with the ethical guideline based on federal regulations and the common rule. Cedars-Sinai Medical Center also has a Federal-wide Assurance. This study was an investigator-initiated study (SC Jordan, M D, Principal Investigator, NCT02134314, FDA IND 15806). The study was designed, conducted, and evaluated solely by the investigators. CSL Behring, LLC (King of Prussia, PA) provided funding and C1INH (BERINERT®). The data in this study were gathered, analyzed and manuscript preparation completed entirely by the investigators all of whom vouch for the results.

Statistical Analysis

Continuous variables are described using means and standard deviations (SDs) or median and interquartile ranges (IQR). Nominal data were expressed as counts and percentages. We compared means and proportions between groups using Student's t-test (or Mann-Whitney test if appropriate) and Fisher exact test. Freedom from dialysis probability according to the treatment (C1INH vs Placebo) was plotted using reverse Kaplan-Meier curves and compared using the log-rank test.

We adopted a Random Forest (RF) analysis to identify prognostic factors predictive of the need for dialysis during the first week and after two weeks post-transplant. We calculated variable importance (VIMP), which measures the increase in prediction error when the variable is "noised-up". A positive value indicates a predictive covariate.

We used STATA (version 14, Data Analysis and Statistical Software) and R (version 3.2.1, R Foundation for Statistical Computing) for the descriptive analyses. All the statistical tests were 2-sided, and probability values <0.05 were considered significant.

Patient Characteristics 70 patients with end-stage renal disease, on dialysis who received deceased donor kidney transplant offers from the United Network for Organ Sharing were assessed for study participation. Patients obtaining a score of >3 (Table 1) were deemed at risk for IRI/DGF and were offered participation in the C1INH study. After consenting, patients were randomized to receive C1INH (N=35) or placebo (normal saline) (N=35) given in the operating room prior to reperfusion of the allograft and repeated 24 hours later (FIG. 1). Patients were monitored for DGF in the first week and for improvements in renal function defined as improvements in eGFR during the first week post-transplant. The characteristics of patients entered into the study are shown in Table 2. Here, no significant differences were noted in the two patient populations. The Kidney Donor Profile Index (KDPI) is predictive of delayed graft function and risk of allograft loss. A KDPI>85% confers the highest risk. This score replaced the older "extended criteria donor (ECD)" and "donor after cardiac death (DCD)" designations that were in place at study initiation. Retrospectively, we determined the mean KDPI scores were 67.71±21.83 in the C1INH group and 64.63±25.39 in the Placebo group (p=0.681). The number of patients with KDPI >85% were similar in the two groups C1INH (n=10 [28.57%] and placebo (n=11 [31.43%]). All patients had pre-implantation biopsies to examine the extent of interstitial fibrosis/tubular atrophy, global sclerosis and vascular changes pre-implantation (Table 2 and FIGS. 2-5). There was no significant difference in pathologic features in the two groups (FIGS. 2-5).

TABLE 2

Characteristics of patients according to the treatment (C1INH vs Placebo).

| | All patients (n = 70) n | | C1INH (n = 35) n | | Placebo (n = 35) n | |
|---|---|---|---|---|---|---|
| Recipient characteristics | | | | | | |
| Age (y), mean (SD) | 70 | 57.9 (9.54) | 35 | 57.66 (7.74) | 35 | 58.14 (11.18) |
| Sex male, no. (%) | 70 | 42 (69.00) | 35 | 20 (57.14) | 35 | 22 (62.86) |
| Diabetes mellitus, no. (%) | 70 | 41 (58.57) | 35 | 21 (60.00) | 35 | 20 (57.14) |
| Black, no. (%) | 70 | 8 (11.43) | 35 | 4 (11.43) | 35 | 4 (11.43) |
| Donor characteristics | | | | | | |
| Age (y), mean (SD) | 70 | 47.37 (14.13) | 35 | 49.17 (12.35) | 35 | 45.57 (15.69) |
| Creatinine (mg/L), mean (SD) | 70 | 1.77 (1.69) | 35 | 1.78 (1.44) | 35 | 1.75 (1.92) |
| DCD donor, no. (%) | 70 | 11 (32.86) | 35 | 11 (31.43) | 35 | 12 (34.29) |
| KDPI, mean (SD) | 70 | 66.17 (23.56) | 35 | 67.71 (21.83) | 35 | 64.63 (25.39) |
| KDPI ≥85, no. (%) | 70 | 21 (30) | 35 | 10 (28.57) | 35 | 11 (31.43) |
| Transplant characteristics | | | | | | |
| Cold ischemia time (h), mean (SD) | 70 | 19.06 (5.54) | 35 | 18.27 (4.89) | 35 | 19.84 (6.10) |
| Immunology at the time of transplant | | | | | | |
| Anti-HLA DSA, no. (%) | 70 | 5 (7.14) | 35 | 3 (8.57) | 35 | 2 (5.71) |
| HLA class of donor-specific anti- HLA antibodies, no. | 5 | | 3 | | | |
| Immunodominant Class I | | 3 | | 2 | | 1 |
| Immunodominant Class II | | 2 | | 1 | | 1 |
| DSA MFI mean (SD) | | 5750 (1425) | | 5000 (1250) | | 6875 (884) |

TABLE 2-continued

Characteristics of patients according to the treatment (C1INH vs Placebo).

|  | All patients (n = 70) n |  | C1INH (n = 35) n |  | Placebo (n = 35) n |  |
|---|---|---|---|---|---|---|
| Treatment at the time of transplant |  |  |  |  |  |  |
| Thymoglobulin, no. (%) | 70 | 53 (75.71) | 35 | 25 (71.43) | 35 | 28 (80.00) |
| Campath, no. (%) | 70 | 17 (24.29) | 35 | 10 (28.57) | 35 | 7 (20.00) |
| Events during the first year |  |  |  |  |  |  |
| ABMR, no. (%) | 70 | 3 (4.29) | 35 | 0 | 35 | 3 (8.57) |
| TCMR, no. (%) | 70 | 5 (7.14) | 35 | 2 (5.71) | 35 | 3 (8.57) |
| Graft loss, no. (%) | 70 | 2 (2.86) | 35 | 1 (2.86) | 35 | 1 (2.86) |
| Death, no. (%) | 70 | 0 | 35 | 0 | 35 | 0 |

Abbreviations: ABMR, antibody-mediated rejection; C1INH, C1 esterase inhibitor; DCD, donor after cardiac death; DSA, donor-specific antibody; KDPI, Kidney Donor Profile Index; MFI, Mean Fluorescent Intensity; SD, standard deviation; TCMR, T cell-mediated rejection.

Primary Outcomes

Figure 6A:
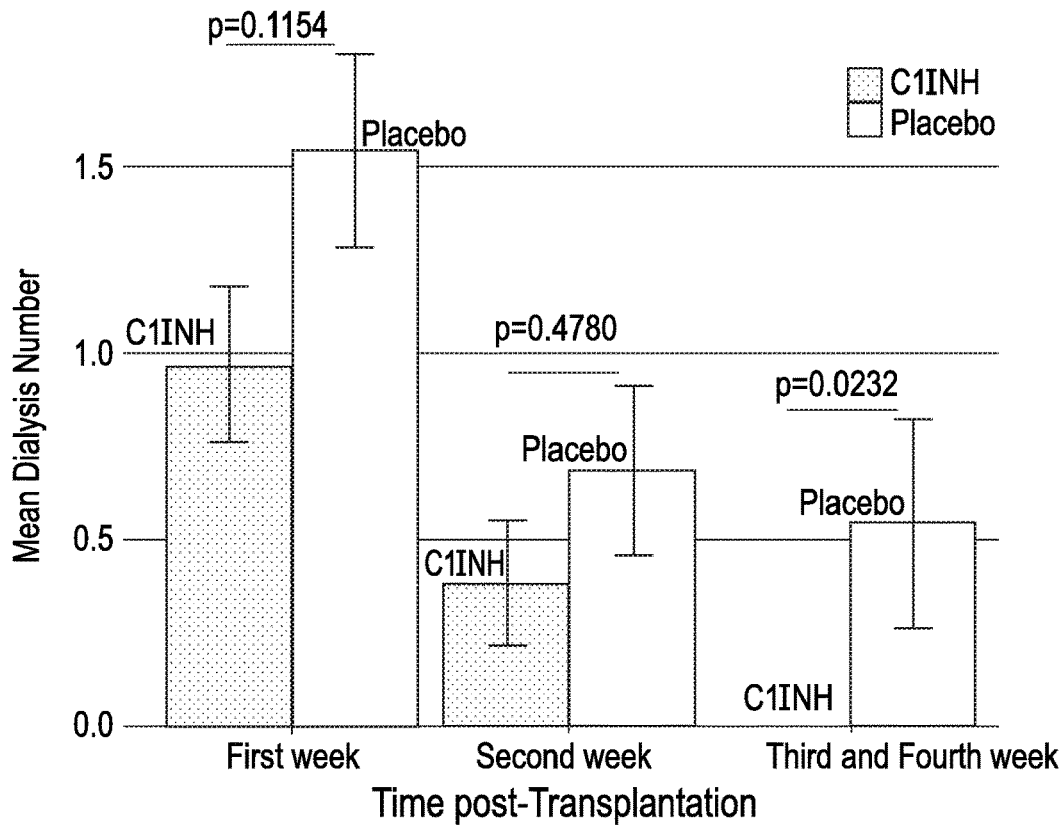
FIG. 6A shows the mean dialysis number during the first week, second week and after two weeks according to the treatment (C1INH vs. Placebo). The T bars indicate standard errors. Here, a significant reduction in the need for dialysis was seen in the C1INH group at 2-4 weeks post-transplant. Abbreviations: C1INH: C1 esterase inhibitor.
Figure 6B:
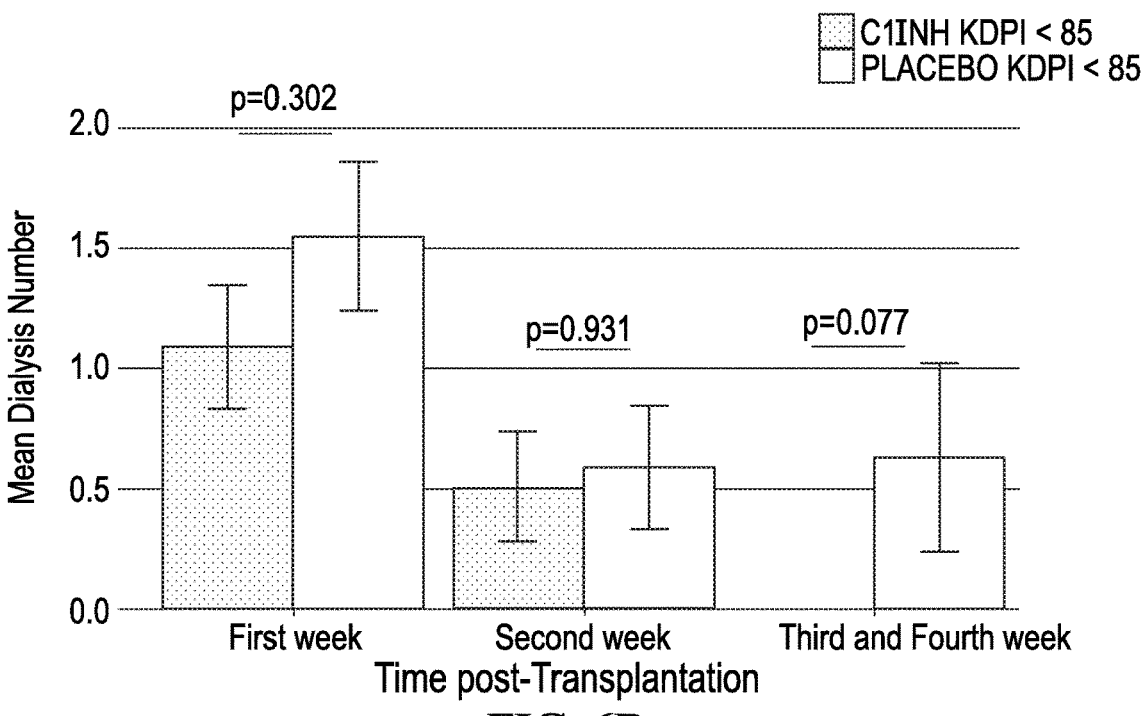
FIG. 6B shows the mean dialysis number during the first week, second week, and after 2 weeks according to the treatment (C1INH vs Placebo). Patients receiving kidney transplants from donors with KDPI scores <85 are shown here. Non-significant decreases in the mean number of dialysis were seen between the C1INH and the placebo groups. The T bars indicate standard errors. C1INH: C1 Inhibitor; KDPI: Kidney Donor Profile Index.
Figure 6C:
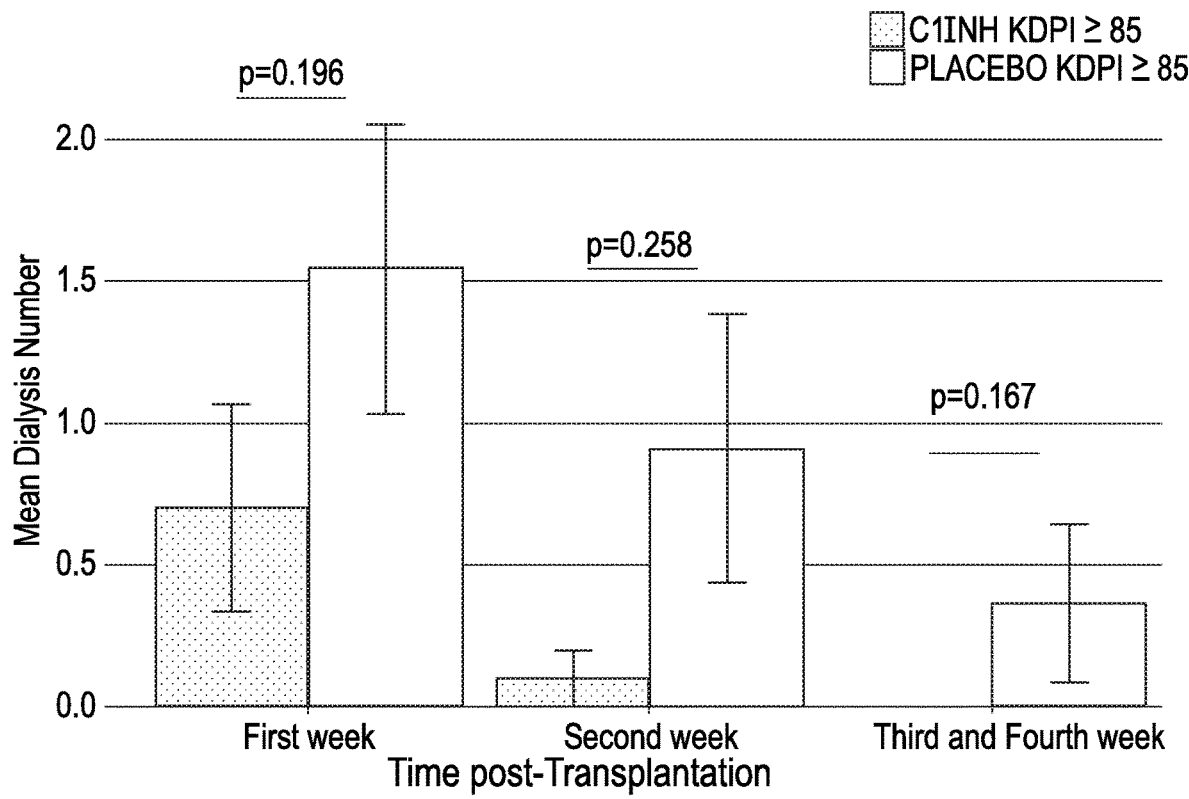
FIG. 6C shows the mean dialysis number during the first week, second week, and after 2 weeks according to the treatment (C1INH vs Placebo) and the KDPI Score. Patients receiving kidney transplants from donors with KDPI scores ≥85 are at increased risk for DGF post-transplant. Here, the mean numbers of dialysis required post-transplant were reduced in the C1INH patients receiving KDPI ≥85 kidneys compared to the placebo KDPI ≥85 group. The T bars indicate standard errors. C1INH, C1 inhibitor; KDPI, Kidney Donor Profile Index.

The need for dialysis during the first week post-transplant did not differ between the C1INH and placebo group (n=15 [44.12%] vs n=21[60.00%], p=0.232; mean number=0.97±1.22 versus 1.54±1.54, p=0.115, respectively) (FIG. 6A). In addition, the eGFR (using MDRD) estimates were also similar in the two groups at one week (C1INH 20.39±17.16 v. placebo 16.20±13.72, p=0.368) Thus, the primary end point was not met. We also examined the need for dialysis based on KDPI scores ≤85 and >85. The data are shown in FIGS. 6B and 6C. Briefly, there was a trend in both groups for C1INH-treated patients to require fewer dialysis sessions with KDPI >85 requiring the fewest.

Figure 7:
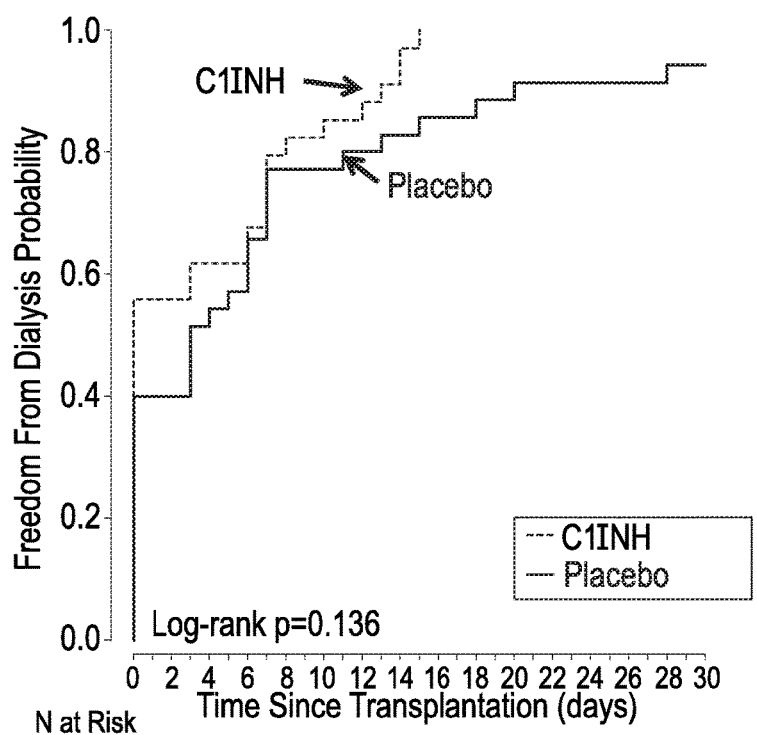
FIG. 7 shows freedom from dialysis probability according to treatment (C1INH vs. Placebo). Briefly, no patients in the C1INH group required beyond 2 weeks post-transplant. Differences did not reach statistical significance.
Figure 8:
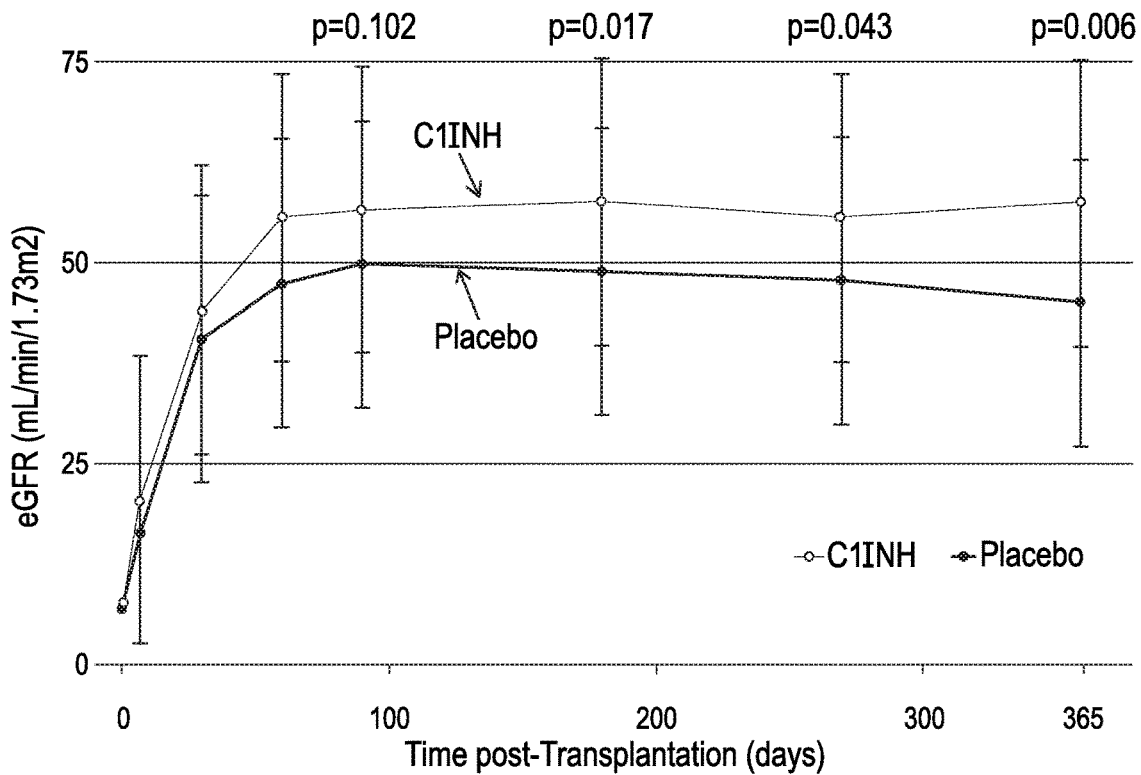
FIG. 8 shows the mean eGFR according to the treatment (C1INH vs Placebo) during the first year. Patients receiving C1INH demonstrated significantly better renal function at 1 year than those receiving placebo at time of transplant. The T bars indicate standard deviations. Abbreviations: C1INH: C1 Inhibitor; eGFR: estimated glomerular filtration rate.
Figure 9:
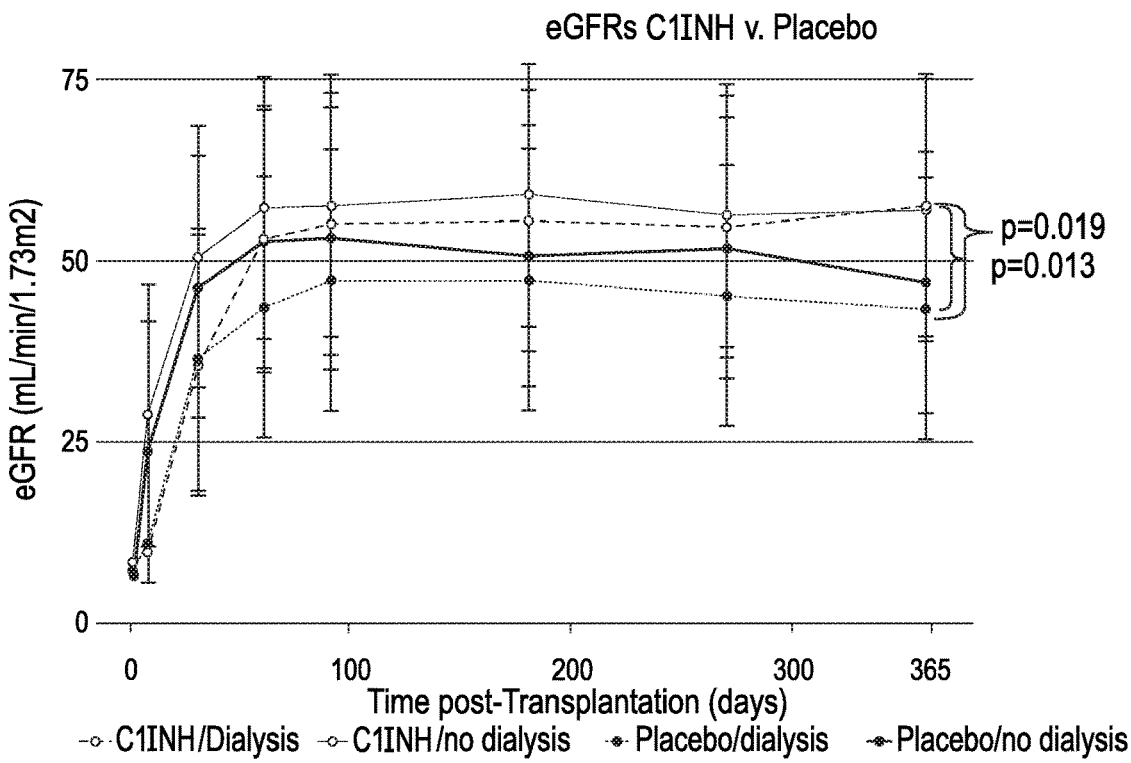
FIG. 9 shows the mean eGFR according to the treatment (C1INH v. Placebo) and the need for dialysis during the first week post-transplant. Significantly higher eGFRs were seen in both C1INH groups compared to the placebo dialysis group. Abbreviations: C1INH: C1 Inhibitor; eGFR: estimated glomerular filtration rate.
Figure 10:
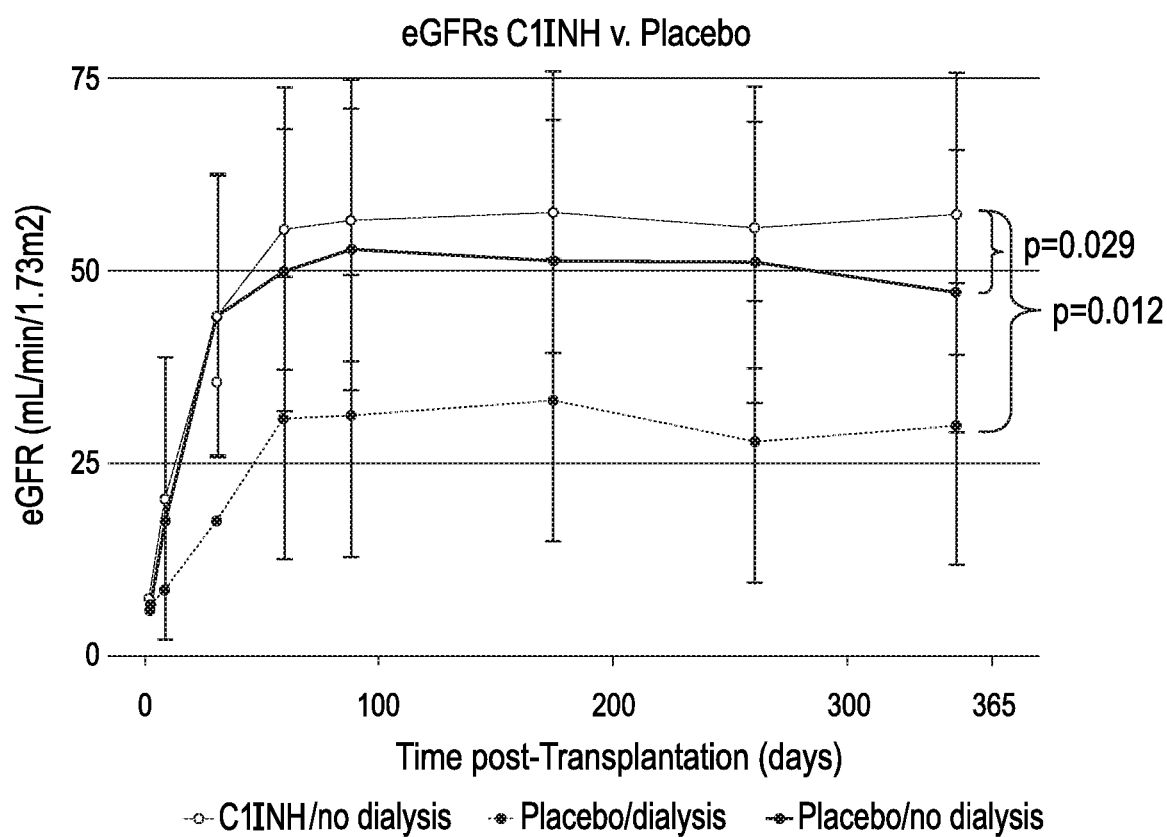
FIG. 10 shows the mean eGFR according to the treatment (C1INH vs. Placebo) and the need for dialysis after two weeks*. Significantly higher eGFRs were seen in the C1INH group compared to the placebo no dialysis and dialysis groups at 1 year. Note that the mean eGFR for the patients in the placebo dialysis group was 29.95 mL/min at 1 year. Abbreviations: C1INH: C1 Inhibitor; eGFR: estimated glomerular filtration rate. * No patients were on dialysis after two weeks in the C1INH group.

However, the need for dialysis was significantly lower in the C1INH group when analysis of those remaining on dialysis 15-30 days post-transplant was done (C1INH mean number of dialysis=0 [n=0] v. placebo mean number of dialysis=0.54±1.65 [n=5; 14.29%] (p=0.023) (FIGS. 6A and 7). We next assessed eGFR values for patients over the first year post-transplant. At one year, the eGFR values for the C1INH group were significantly higher (C1INH 57.33±15.77 v. placebo44.90±20.52, (p=0.006) (FIG. 8). FIG. 9 shows the eGFRs for the C1INH and placebo groups by requirements for dialysis during the first 7 days post-transplant. Patients are divided into four groups: C1INH+ dialysis (n=15), C1INH–dialysis (n=19), placebo+dialysis (n=21) and placebo–dialysis (n=14). The eGFRs for C1INH+dialysis and –dialysis are similar and not different from the placebo–dialysis at one year (C1INH–dialysis vs placebo–dialysis, p=0.170). However, the eGFRs at 12 months are significantly better for the C1INH+dialysis 57.69±16.58 v. placebo+dialysis group 43.44±17.35 (p=0.019). FIG. 10 shows the eGFRs for the C1INH and placebo groups by requirements for dialysis during day 15-30 post-transplant. Here, no patients in the C1INH group were on dialysis. eGFRs were significantly better in the C1INH–dialysis (n=34) group v. placebo–dialysis (n=30) group (57.33±15.77 v. 47.39±19.71 (p=0.029). More importantly, the eGFR for the placebo+dialysis group was 29.95±20.93 mL/min at 1 year. Using a RF analysis, we defined the variables most associated with the need for dialysis. During the first 2 weeks posttransplant, these included DCD donors, KDPI ≥85, and C1INH use (C1INH associated with less dialysis). The variables associated with need for dialysis between the third and fourth week were C1INH (C1INH associated with less dialysis), donor's age, and DCD donors.

Figure 11:
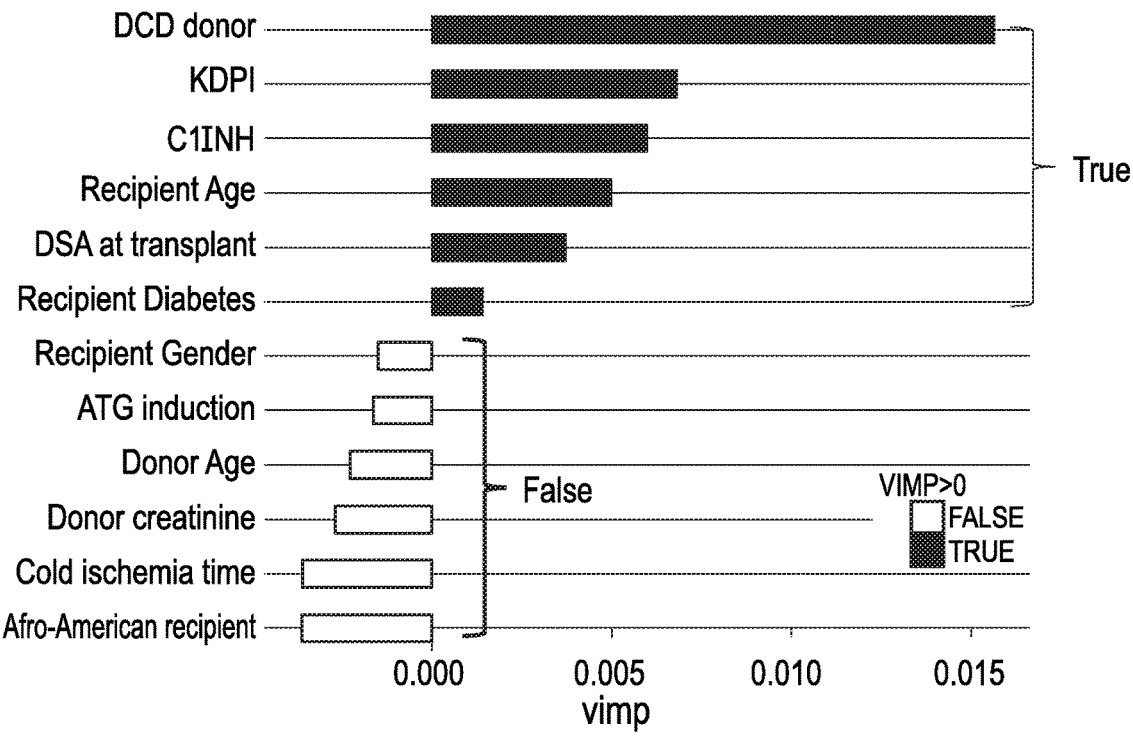
FIG. 11 shows random forest evaluation of the relative importance of clinical and immunological variables for predicting need for dialysis during the first week. Here, analyses of variables in order of importance that predict the need for dialysis are DCD donor status, KDPI score and C1INH therapy. Abbreviations: C1INH: C1 Inhibitor; KDPI: Kidney Donor Profile Index; DSA: Donor specific antibody; ATG: Anti-thymocyte globulin.
Figure 12:
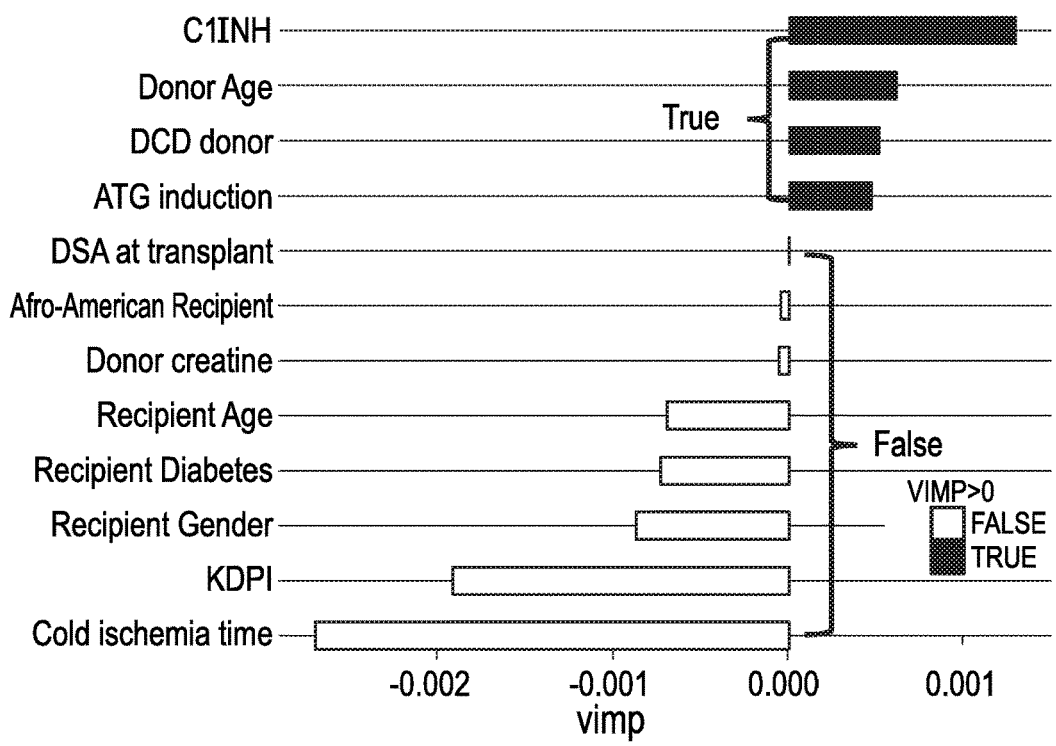
FIG. 12 shows random forest evaluation of the relative importance of clinical and immunological variables for predicting need for dialysis after two weeks. C1INH therapy status was the most important variable predicting freedom from dialysis after 2 weeks. Factors shown in red (false) had no impact of the risk for remaining on dialysis after transplantation. Abbreviations: C1INH: C1 Inhibitor; KDPI: Kidney Donor Profile Index; DSA: Donor specific antibody; ATG: Anti-thymocyte globulin.
Figure 13:
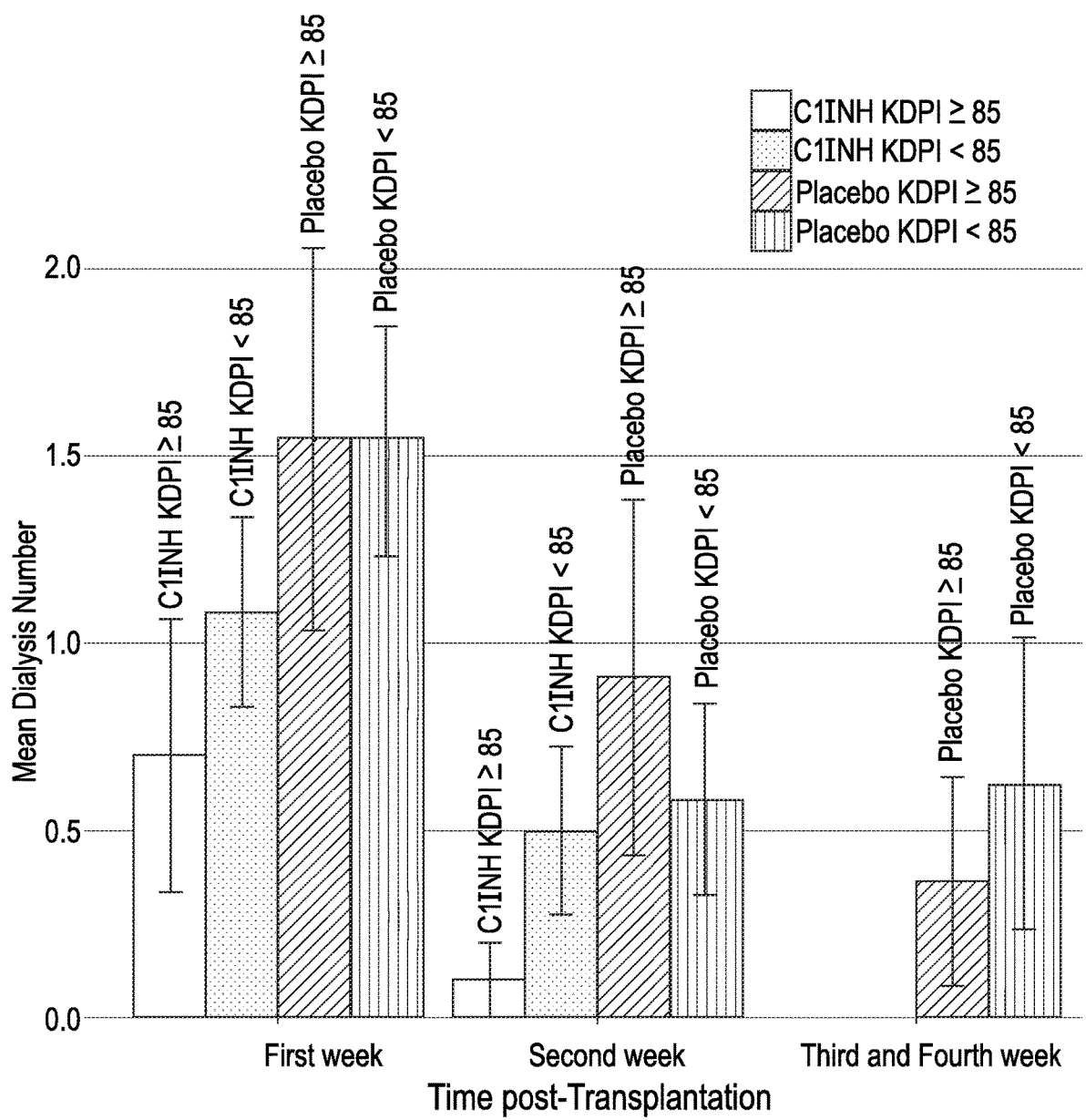
FIG. 13 shows the mean dialysis number during the first week, second week and after two weeks according to the treatment (C1INH vs. Placebo) and the KDPI Score. Patients receiving kidney transplants from donors with KDPI scores >85 are at increased risk for DGF post-transplant. Here, the mean number of dialysis required post-transplant were reduced in the C1INH patients receiving KDPI >85 kidneys compared to the placebo KDPI >85 group. The T bars indicate standard errors. Abbreviations: C1INH: C1 Inhibitor; KDPI: Kidney Donor Profile Index. A higher KDPI is indicative of older donor and greater risk of injury.
Figure 14:
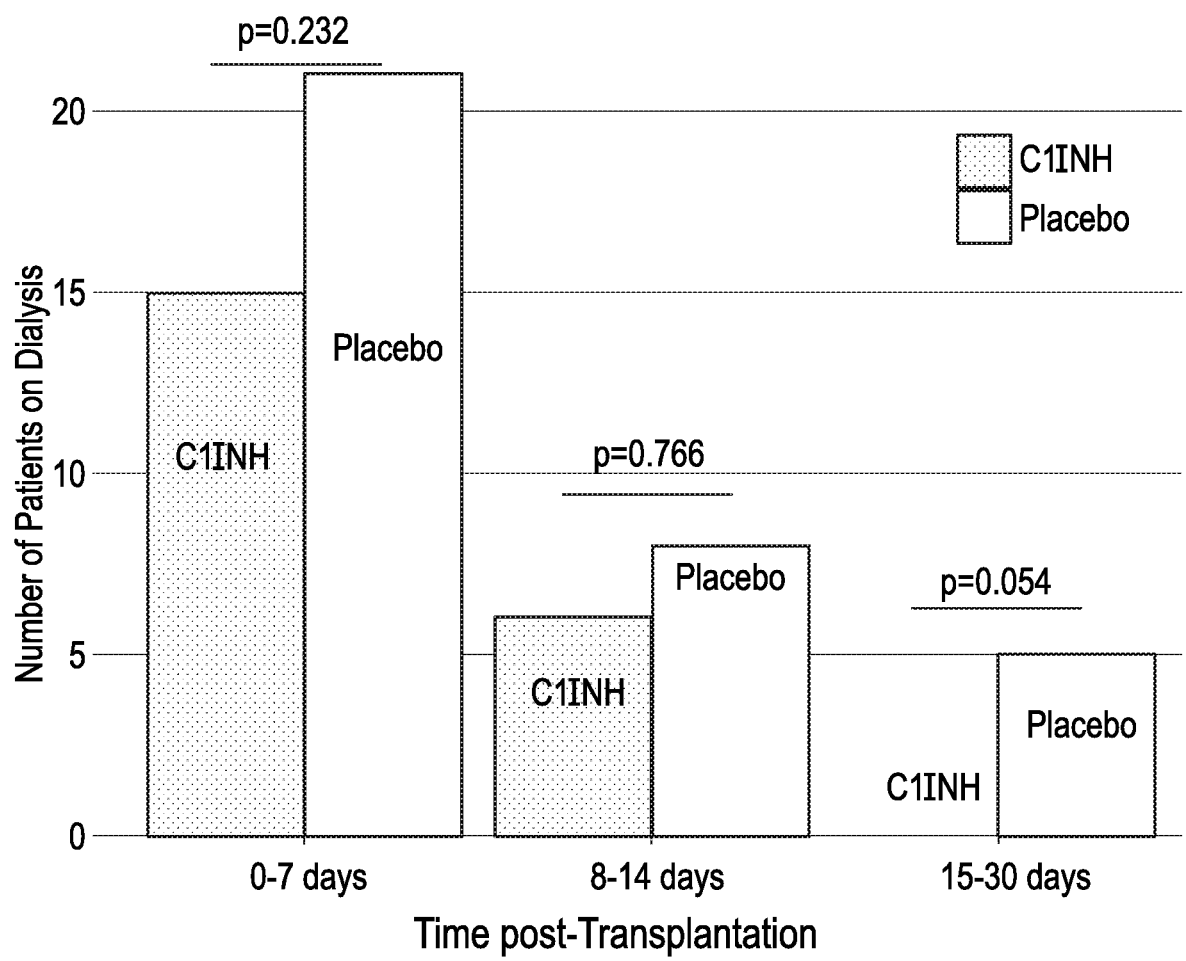
FIG. 14 depicts in accordance with various embodiments of the invention, number of patients on dialysis during the first week, second week and after two weeks according to the treatment (C1INH vs. Placebo). Abbreviations: C1INH: C1 Inhibitor.
Figure 15:
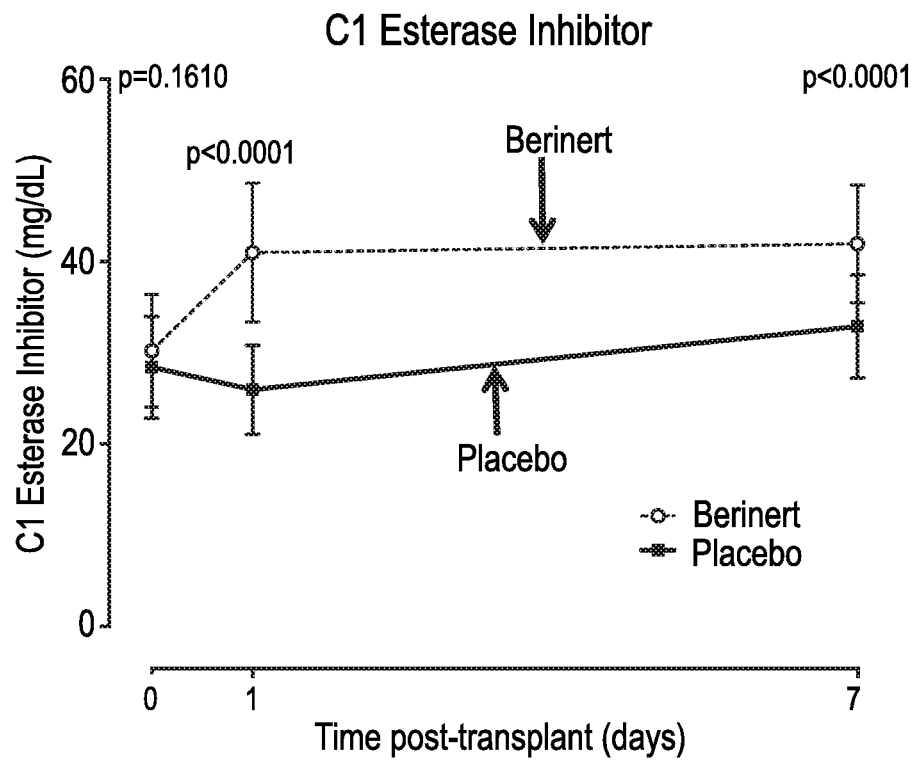
FIGS. 15-21 depict in accordance with various embodiments of the invention, safety labs in C1INH vs. placebo groups in which the following safety labs were analyzed: C1 esterase inhibitor (FIG. 15), Complement 3 (C3) (FIG. 16), Complement 4 (C4) (FIG. 17), International Normalized Ratio (INR) (FIG. 18), D-dimer (FIG. 19), fibrinogen (FIG. 20), and partial thromboplastin time (PTT) (FIG. 21). C1 esterase inhibitor levels are significantly higher than placebo controlled group as expected (p<0.0001). No statistical differences in C3, C4, INR, D-dimer, fibrinogen, and PTT levels were observed in the C1INH v the placebo controlled groups.
Figure 16:
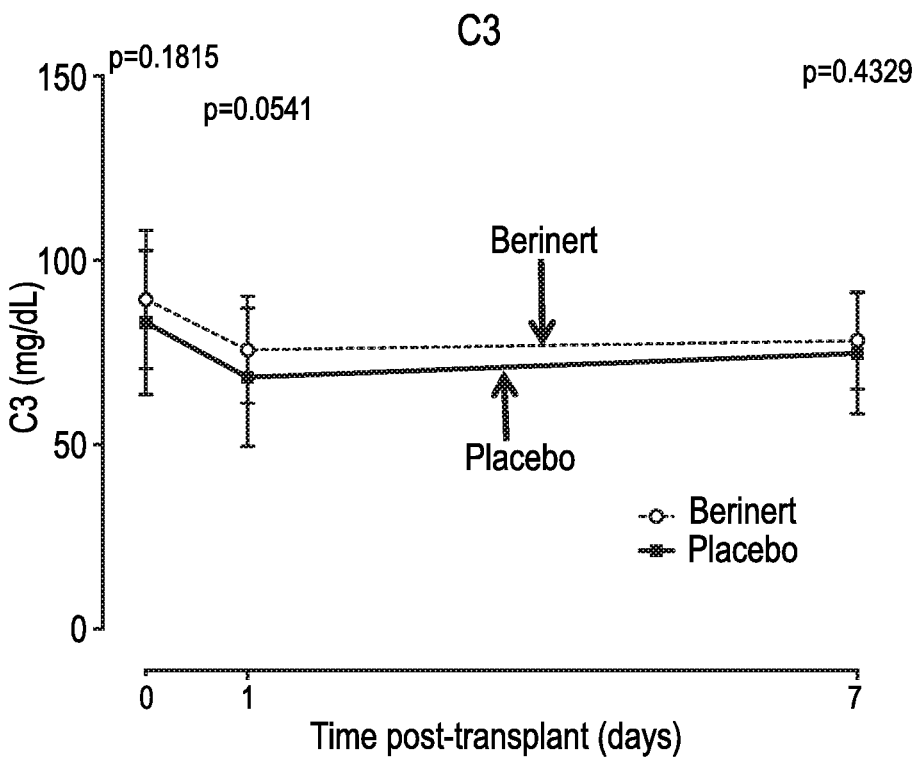
Figure 17:
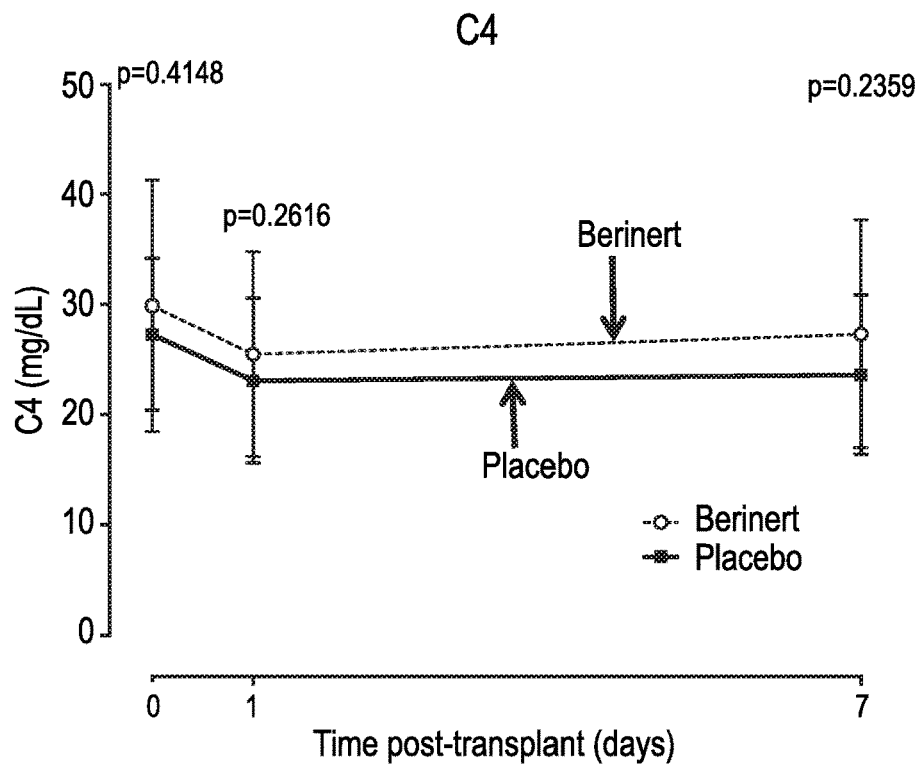
Figure 18:
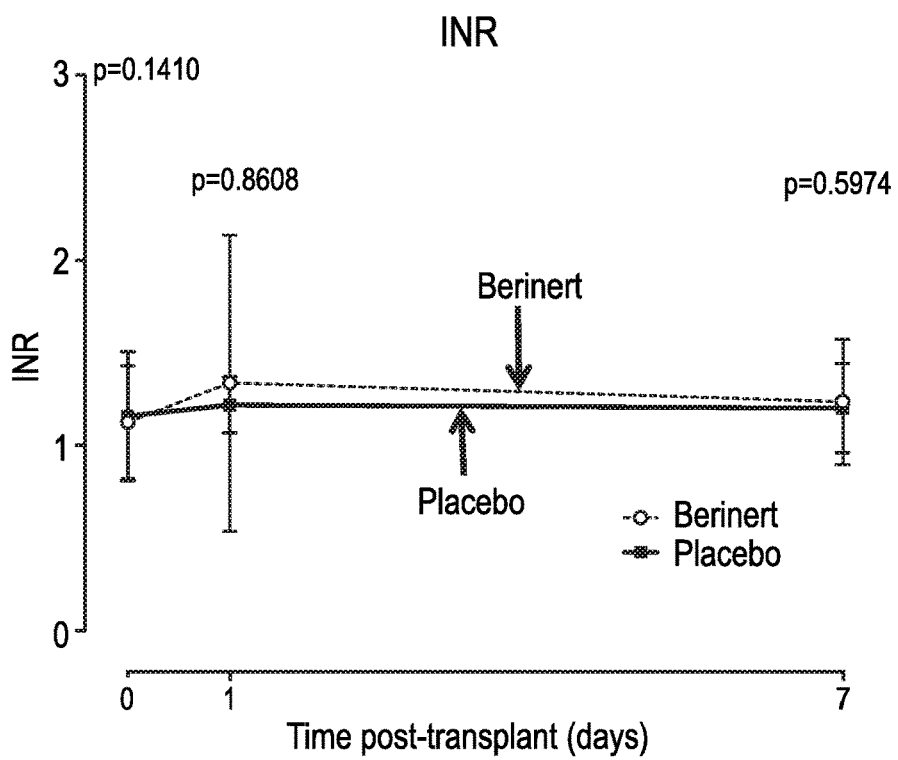
Figure 19:
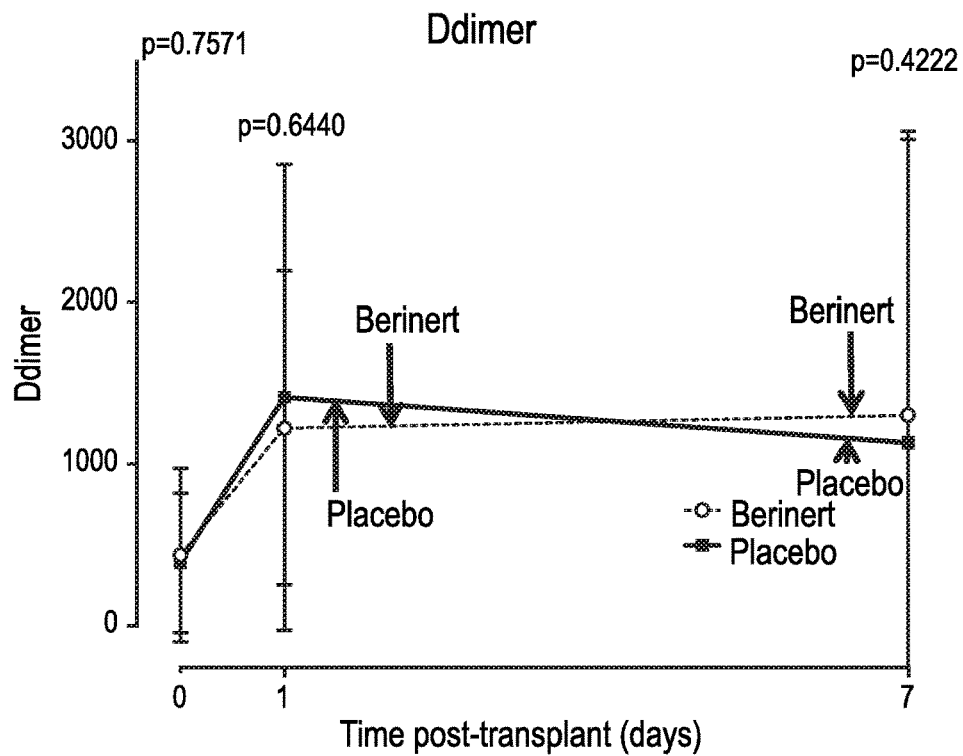
Figure 20:
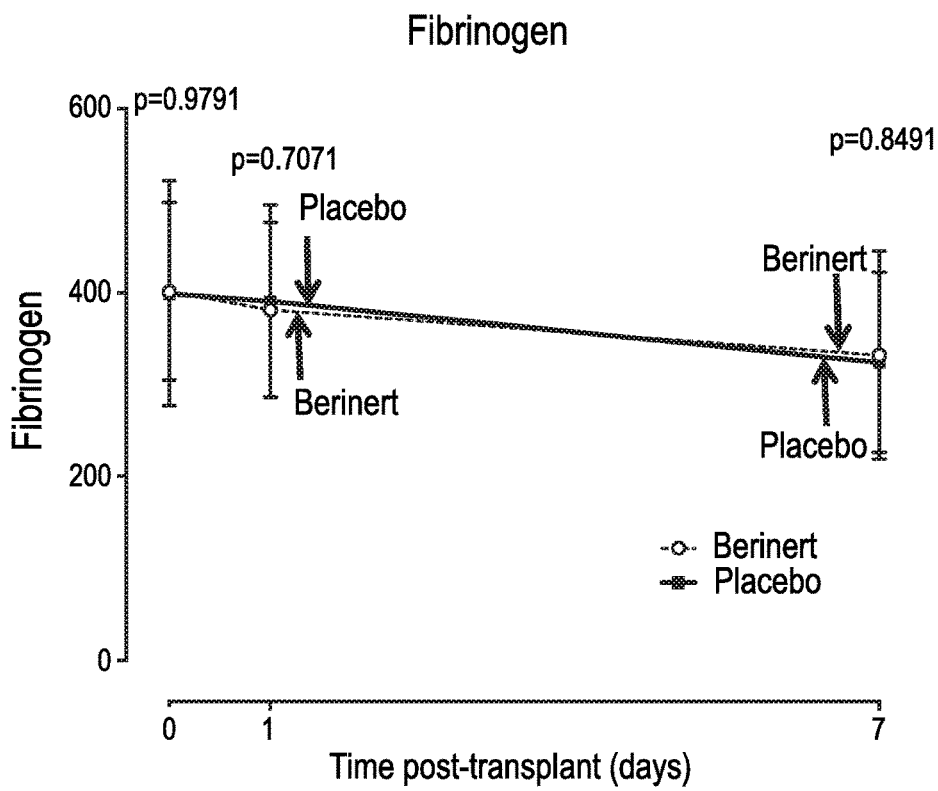
Figure 21:
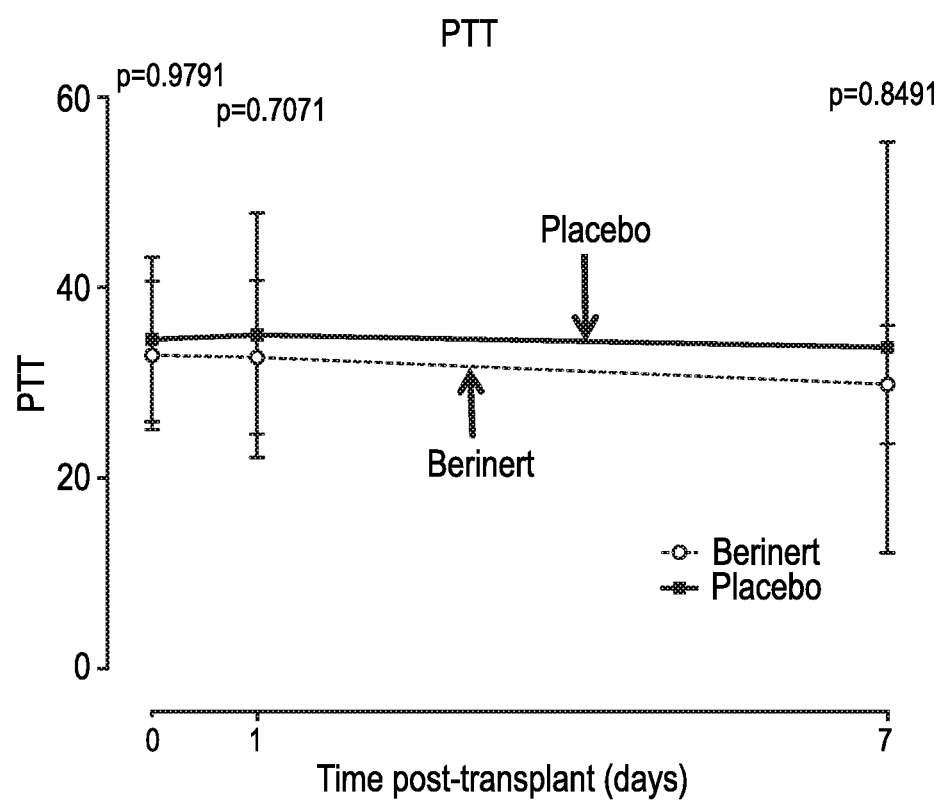

Thus, C1INH appeared to confer a benefit in reducing the need for dialysis post-transplant and improved renal function at 12 months post-transplant compared to controls. Statistical analyses of factors relating to freedom from dialysis are shown in FIGS. 11 and 12. Analysis of the composite end point of death, graft loss, and rejection revealed a non-statistically significant difference with numerically fewer events in the group receiving the C1INH. Here, C1INH exerts the strongest effect considering patients remaining on dialysis for 2-4 weeks.

Secondary Outcomes

There were no differences in patient and graft survival at 1 year (p=0.493). Two grafts were lost in the placebo group and one in the C1INH group. There were no patient deaths. One patient (C1INH) was removed from study analysis due to development of a significant post-transplant bleed that led to acute kidney injury in a functioning allograft. This was not considered to be related to the C1INH. We also assessed a number of biochemical parameters. C1INH levels were significantly higher in the treatment group, and this persisted at one week post-transplant. Levels of C3, C4, fibrinogen, PT=Prothrombin Time/PTT=Partial Thromboplastin Time, and d-dimers were similar in the two groups (FIGS. 15-21). C1 esterase inhibitor, Complement 3 protein (C3), and Complement 4 protein (C4) were analyzed from transplant day 0 to post transplant day 7. C1 esterase inhibitor levels were significantly increased in the C1INH vs placebo group (p<0.0001) on days 1 and 7 post-transplant. There were no significant differences in C3 and C4 levels up to day 7 post-transplant. International Normalized Ratio (INR), Pro-thrombin time (PTT), D-dimer protein (D-dimer), fibrinogen were analyzed from transplant day 0 to post transplant day 7. There were no significant differences in INR, PTT, D-dimer, and fibrinogen levels between C1INH vs placebo group up to day 7 post-transplant.

Safety Assessments

Twenty patients (28.6%) experienced serious adverse events (SAE)s, ten from C1INH and ten from the placebo group. Some patients experienced more than one SAE. Sixteen SAEs were noted in the placebo group vs. eleven in C1INH group. All SAEs resolved with treatment and were deemed not to be related to C1INH. A complete summary of SAEs is shown in Table 3.

TABLE 3

*Same patient may have one or more serious adverse event listed.

| Serious Adverse Event | C1INH (N = 10) | Placebo (N = 10) |
|---|---|---|
| Infection | ESBL UTI/Bacteremia (1) Fever/Neutropenia (1) Viral Infection (1) Purulent Drainage from Wound (1) | Fever(1), Sepsis from UTI (1) Acute Encephalopathy/Right lower lobe pna (1) |
| Endocrine | Diabetic Ketoacidosis (1) | — |
| Respiratory | Flash pulmonary edema (1), Dyspnea on Exertion(1) | — |
| Circulatory/ Cardiovascular | Afib (1), Shortness of breath/Chest Pain (1), Non ST Segment Elevation (1) | Right Leg DVT (1), Upper extremity and facial swelling/ SVC syndrome (1), Aflutter (1), Afib/ Vtach (1), HTN (1) |
| Renal/urologic | Elevated Cr/Swelling (1) | Nephrectomy d/t poor perfusion (1) Urine Leak (1), Perirenal transplant hematoma (1), Dysuria(1) |
| Gastro- intestinal | Abdominal pain(1) | Abdominal Pain/ Vomiting (2) Nausea/Vomiting (1) |
| Neurologic | — | Slurred speech/ weakness/fatigue (1) |
| Total # of events | 12 | 16 |

Afib, atrial fibrillation; Aflutter, atrial flutter; C1INH, C1 esterase inhibitor; Cr, creatinine; DVT, deep vein thrombosis; HTN, hypertension; pna, pneumonia; SVC, Superior vena cava; UTI, urinary tract infection; VTach, ventricular tachycardia. Same patient may have 1 or more serious adverse events listed.

Additional safety concerns with C1INH were risk of meningococcal infection and venous thromboembolisms. Safety measures per protocol included meningococcal vaccination at time of transplant, administration of prophylactic ciprofloxacin for thirty days post-transplant, and assessment of venous thromboembolisms for the study duration using Well's criteria. No meningococcal infections were seen. One patient in the placebo group developed venous thromboembolism which resolved with treatment.

At the 1-year assessment, there were three graft losses. One occurred in the placebo arm (one due to antibody mediated rejection), and one in the C1INH arm (surgical complication). The graft loss in the C1INH group was due to repeated retroperitoneal hematomas with acute kidney injury (AKI) due to bleeding from a pseudoaneurysm of the iliac artery-renal artery anastomotic site. After treatment, the patient regained normal renal function for 4 months, but again developed AKI episodes. The patient subsequent lost her graft 9 months post-transplant related to a biopsy complication.

The detrimental impact of IRI-induced DGF on cost and long-term function and survival of kidney allografts is well documented. This has also come into clearer focus with the implementation of the new KAS, which increases the risk for DGF, especially in older recipients. Recent data from Kumar and colleagues explored the cellular and molecular pathways responsible for renal repair after ischemic kidney injury. In a mouse model of IRI, these investigators demonstrated that a single ischemic episode resulted in the activation of genes associated with innate and adaptive immunity and fibrosis that resulted in progression to chronic kidney disease at 1 year post-IRI. Despite identification of multiple targets for intervention, altering the natural history of IRI and DGF has remained elusive. However, animal models indicate that reduction or inhibition of complement activation may represent an important therapeutic target for intervention.

The complement system is a critical component of the innate immune system, but also has an important role in recognizing damage-associated molecular patterns (DAMPs) associated with ischemic injury. Other reports indicate that C1INH treatment can prevent IRI in experimental models. Dalle Lucca et al showed that recombinant human C1INH (rhC1INH) ameliorated tissue injury in a porcine model of hypotension due to controlled hemorrhage. Administration of rC1INH significantly reduced IRI injury to kidneys attributable to IRI-induced complement activation. Treated animals also showed reduced immune cell infiltration and cytokine production. Using a swine model of IRI injury to kidneys, Delpach et al. found that IRI was associated with C3 activation, through the MBL/MASP-2 pathway. Infusion of C1INH led to significant reductions in peritubular capillary C4d deposition and C5b-C9 MAC deposition. C1INH also reduced infiltrating immune cells. Animals treated with C1INH had significantly less interstitial fibrosis/tubular atrophy and loss of renal function. Danobeitia et al. also demonstrated a significant inhibitory effect of C1INH on ischemia-induced AKI and fibrosis in a mouse model. Here, the investigators demonstrated a protective effect mediated by C1INH in the prevention of AKI after ischemic insult. Pretreatment with C1INH prior to induction of IRI inhibited complement activation, prevented C5a generation, and downregulated the subsequent inflammatory response. This included the inhibition of cytokine release (interleukin 6), decreased infiltration of macrophages and neutrophils, and decreased production of profibrotic cytokines. Thus, the progression to fibrosis after ischemia was limited by C1INH-induced reduction in the initial inflammatory injury. This study provides further evidence to support a central role for early complement activation, primarily through the MBL/MASP-2 pathway, in the transition from inflammatory injury to interstitial fibrosis and tubular atrophy. It also indicates the importance of early inhibition of complement directed pathways for prevention of tubulo-interstitial fibrosis. The authors conclude that their work provides support for C1INH as an attractive therapeutic option for the management of acute and chronic ischemic renal conditions predisposing to kidney fibrosis.

Data presented here in a balanced at risk patient population show that C1INH therapy given intraoperatively and 24 hours post-transplant demonstrated significant benefits in reducing the need for hemodialysis after the second week post-transplant and, more importantly, was associated with significantly better renal function at 1 year. Subset analysis showed that patients in the placebo group who remained on dialysis for 2-4 weeks post-transplant had a mean eGFR of 29.77±19.14 at 1 year compared to C1INH treated patients (60.32±14.75 mL/min)(p=0.02) (FIG. 10).

The patient population was balanced between the 2 groups, and donor organ characteristics, including implantation biopsies, were similar. We also believe this study establishes the need to focus on long-term outcomes such as eGFR at 1 year rather than on early events such as need for dialysis and changes in serum creatinine in the first week post-transplant.

Example 3

The Food and Drug Administration (FDA or Agency) provided a draft guidance to assist sponsors in the clinical development of drugs for the prevention of delayed graft function (DGF) in kidney transplantation. The purpose of the guidance is to assist sponsors in the clinical development of drugs for the prevention of delayed graft function (DGF) in kidney transplantation.

A. General Considerations

1. Efficacy Considerations

Trials should be superiority trials in which an active treatment is compared to placebo because there is no approved drug for the prevention of DGF and there is no standard of care that has been demonstrated to be effective.

If the drug is a new drug (i.e., not approved by the FDA for any use), two adequate and well-controlled trials generally are recommended to provide evidence of effectiveness. A single adequate and well-controlled trial supported by other independent evidence, such as a trial in a closely related indication (e.g., based on mechanism of action, target receptor), could potentially provide evidence of effectiveness in the prevention of DGF. A single adequate and well-controlled trial may be appropriate if the results of efficacy are highly robust. Sponsors should discuss with the FDA other independent confirmation that would be used to support the highly significant findings from a single adequate and well-controlled trial in prevention of DGF.

2. Safety Considerations

In general, it is recommended a preapproval safety database of 300 patients or more on the investigational drug. If the same or greater dose and duration of therapy for the prevention of DGF were used in clinical trials for other disease indications, the safety information from those clinical trials can be part of the overall preapproval safety database.

For new drugs that have an important clinical benefit compared to current management strategies, depending on the benefit demonstrated, a smaller preapproval safety database may be sufficient. Sponsors should discuss the appropriate size of the preapproval safety database with the FDA during clinical development.

B. Specific Efficacy Trial Considerations

1. Study Design, Randomization, Stratification, and Blinding

The clinical trial population for efficacy trials should include male and female de novo kidney transplant recipients, representative of a U.S. patient population, including race, age, sex, and other baseline characteristics.

The type of donors, preferably graded by the kidney donor profile index implemented by the new Kidney Allocation System, should be specified in the protocol. Consideration should be given to stratifying the study enrollment, for example, based on study center and/or the type of induction treatment (if there is more than one). If recipients of the DCD donor kidneys or donor kidneys preserved by machine perfusion are planned to be enrolled, stratification based on the type of donor (DCD versus DBD) and organ preservation method is highly recommended.

The studies should be randomized and blinded.

2. Study Population and Specific Populations

Enrichment strategies can be used to select the study population at a higher risk for developing DGF compared to the overall kidney transplant recipient population for these clinical studies, as discussed in the draft guidance for industry Enrichment Strategies for Clinical Trials to Support Approval of Human Drugs and Biological Products.

3. Entry Criteria

The protocol should specify the inclusion and exclusion criteria that will be used to select patients to participate in the clinical study, including any enrichment strategies.

4. Organ Storage Conditions and Use of Concurrent Immunosuppressants and Other Medications The protocol should specify the type of organ recovery, storage, and transport conditions: machine perfusion (cold or warm) or static cold storage.

Immunosuppressive (IS) therapy after transplantation should be specified, including the induction agent(s) and the maintenance therapy. In clinical trials of DGF, it is highly recommended that the type of induction, including the initial intravenous corticosteroid boluses at the time of transplantation, and the maintenance IS therapy be standardized across the treatment groups to minimize the potential confounding effect of these factors on the study endpoints.

The protocol should state that data on the IS and other medications used in the study patients should be collected on the case report forms (CRFs). For drugs managed using therapeutic drug monitoring, drug trough levels should be collected on the CRF.

5. Dose Selection

Dose-ranging studies should be conducted during phase 1 or phase 2 testing. Generally, studies to prevent DGF (and other forms of early graft dysfunction) would be expected to have a short duration of treatment, so different dosage regimens could be evaluated in the first week after transplantation.

6. Choice of Comparators

Placebo-controlled studies are recommended, because at present there are no approved therapies and no standard of care for the prevention of DGF.

7. Efficacy Endpoints a. Primary Efficacy Endpoint

Sponsors should consider the following when choosing a primary efficacy endpoint:

Short-term assessment or composite endpoint

Short-term assessment of the graft function for efficacy—
In the short-term assessment of the graft function, the common definition of DGF (i.e., the requirement for hemodialysis treatment within the first 7 days following transplantation) can be used as the primary endpoint. Other definitions of DGF supported by literature also can be proposed.

As an alternative to the assessment of the occurrence of DGF as a binary endpoint, DGF severity scoring systems can be proposed. These can include the number of hemodialysis sessions required until recovery of renal function or time to recovery of renal function after the diagnosis of DGF. If the DGF severity scoring endpoint is chosen as the primary endpoint, a justification for the clinical significance and relevance of the proposed score difference should be provided.

In addition to recording any hemodialysis sessions during the first 7 days post-transplant, information on hemodialysis sessions after Day 7 until post-transplant Day 30, regardless of the reason for dialysis, should be collected on the CRFs to evaluate the durability of treatment, and submitted in the final study report.

Short-term composite endpoint using SGF and fDGF—
Another option is to select a short-term primary endpoint that includes DGF as well as some component of SGF or fDGF. The protocol should include the specific definition of SGF and fDGF. As noted above, the use of severity scoring systems for these outcomes should be specified, and the prospectively defined difference in scores should be justified as clinically meaningful.

Long-term efficacy and improved renal function—If the goal of the clinical study is to demonstrate that the drug leads to an overall sustained improvement in renal function, compared to placebo, then renal function data need to be collected for all patients for a minimum of 12 months. A clinically meaningful difference in renal function (assessed using serum creatinine levels or glomerular filtration rate), should be justified.

b. Secondary Efficacy Endpoints

Sponsors should consider the following when choosing secondary efficacy endpoints:

DGF—If one of the DGF severity scoring methods is chosen for the primary endpoint, the classic definition of DGF (i.e., requirement of dialysis within the first 7 days following transplantation) should be among the secondary endpoints Day 30 analysis—The purpose of this analysis is to evaluate the durability of treatment effect after the first week post-transplant Renal function—The comparison of renal function (measured or calculated) between the treatment and placebo arms at prespecified time points for 12 months following transplantation should be among the secondary endpoints 8. Safety Considerations Because dosing is expected to occur during the first week post-transplantation, routine laboratory testing and collection of adverse event data attributable to the drug likely can be evaluated with 30 days of follow-up. Depending on the pharmacokinetic/pharmacodynamic (PK/PD) properties of the drug, longer clinical and laboratory follow-up for drug-associated adverse events may be needed.

As noted above, the primary efficacy endpoint can be evaluated when data are available for the first 30 days post-transplant. However, additional follow-up is needed to understand the long-term effect of a drug to prevent DGF on the kidney allograft and patient.

For this indication, the mechanism of action of the drug is related to preventing injury and inflammation. The primary mechanism of action is not as an immunosuppressant (these drugs are not primarily intended to suppress T-cells and B-cells, per se). However, one cannot assume the drug for DGF is neutral with respect to IS or other related effects (low white blood cell, cytomegalovirus pneumonia). Therefore, acute rejection, graft loss, and death are not efficacy endpoints; rather, they are safety endpoints in trials of drugs to prevent DGF. The reason for longer follow-up is to assess whether the DGF drug has some unintended effect on the kidney allograft (toxicity), and whether that toxicity affects the kidney's ability to function, making it susceptible to rejection or other injury and affecting survival (either favorably or adversely). The general duration of follow-up for safety should be a minimum of 12 months, and information should be collected on the survival and function of the graft (including episodes of rejection), the occurrence of hospitalization, and patient survival at a minimum at Month 3 (approximately Day 90), Month 6, and Month 12, as follows:

Patient and graft survival—Patient and graft survival data should be among the safety endpoints, and data for at least 12 months after transplantation should be collected Rejection—Acute cellular rejection and antibody mediated rejection episodes should be recorded on the CRFs for at least 12 months following transplantation and analyzed as part of the safety endpoints Hospitalizations—Data on hospitalizations should be collected for at least 12 months post-transplantation and analyzed as part of the safety endpoints 9. Study Procedures and Timing of Assessments The primary endpoint can be assessed at Day 7 after transplant. The need for dialysis between Day 7 and Day 30 should also be evaluated, including the number of dialysis sessions captured on the CRF, for assessment of the durability of treatment effect.

To evaluate the comparability of the study groups, dialysis sessions in the week before transplant should be captured on the CRF.

Likewise, for the assessment of safety, information on all adverse events and laboratory tests should be collected for up to Day 30 for drugs with short half-lives. However, depending on the PK characteristics and duration of PD effect, longer follow-up with collection of laboratory data and adverse event assessments may be needed.

Data on the following types of serious adverse events should be collected for a minimum of 12 months: acute rejection, graft loss, hospitalizations (e.g., for infection, new onset diabetes after transplantation, neurologic adverse events, malignancies), and patient death. All attempts should be made to collect these data; missing information on hospitalizations or acute rejection should be minimized. Long-term safety evaluation should be collected at a minimum at Month 3, Month 6, and Month 12.

10. Endpoint Adjudication

There should be no endpoint adjudication, meaning that for the intent-to-treat (ITT) analysis, all dialysis sessions that occurred within the first 7 days after transplantation should be included in the analysis. However, sponsors can perform sensitivity analyses to look at subsets of patients where the specific reason for the dialysis session (e.g., hypervolemia) is taken into consideration. These analyses can be done in addition to the ITT population analysis but should not replace it.

11. Statistical Considerations

The protocol should specify how information will be collected and how it will be analyzed. All patients with DGF, defined as dialysis within 7 days of transplant, should be included as treatment failures in the analysis. Patients who experience graft loss, or death or are lost to follow-up in the first 7 days should be imputed as treatment failures. However, no patient should be lost to follow-up in the first 30 days after transplant.

The primary efficacy endpoint should be analyzed based on the ITT population, defined as all patients randomized who receive a kidney transplant.

If the protocol specifies SGF or PDGF as part of the primary composite endpoint, the planned analysis should be specified in the protocol and statistical analysis plan (SAP). Strategies to handle missing data should be defined; however (as noted above), there should be no missing data in the first 30 days after transplant.

If other measures of treatment success, such as severity scores or time to graft function recovery, are used as the primary endpoint, the protocol and SAP should describe how the results will be analyzed. For patients who experience graft loss or death in the first 30 days, an appropriate analysis strategy should be defined (e.g., imputing three dialysis session per week should be considered when actual data are not available).

For the secondary endpoint, a Day 30 analysis should look at the percentage of patients who received dialysis within the first 30 days post-transplant, using similar analysis strategies as for the primary endpoint. This analysis is to assess durability of the treatment. The direction and magnitude of the treatment effect should be comparable to the primary endpoint.

Safety should be analyzed in those ITT patients who received at least one dose of study drug or control drug (e.g., placebo) and were evaluated for acute rejection, graft loss, hospitalization for serious adverse reactions, and patient death at least at Month 3, Month 6, and Month 12.

12. Accelerated Approval (Subpart H) Considerations

To be considered for accelerated approval, the new drug application (NDA) or biologics license application (BLA) should be submitted with efficacy data and at least 3 months (90 days) of safety data for all patients. In this original submission, some patients should already have been followed for longer than 90 days. Safety data collected on acute rejections, graft loss, hospitalizations for serious adverse reactions, and death between Month 3 and Month 6 should be submitted in the 120-day safety update along with an integrated presentation of the Month 6 safety data (patient data in the original NDA or BLA and patient data in the 120-day safety update).

For full approval, information on acute rejections, graft loss, hospitalizations for serious adverse reactions, and death for a minimum of 12 months post-transplant should be submitted as part of the original NDA or BLA submission, or as a postmarketing requirement under accelerated approval. Additional details of the clinical trial design can be discussed during drug development.

13. Risk-Benefit Considerations

The early benefit of preventing DGF should be compared to the safety of the drug, evaluated directly in the first 30 days post-transplant and the effect, if any, on the subsequent rates of acute rejection, graft loss, serious adverse reactions requiring hospitalization, and patient death for a minimum of 12 months after transplantation. The benefit of preventing DGF should outweigh the risks of treatment. The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method for reducing the likelihood of delayed kidney allograft function and improving allograft kidney function at about one year following transplantation in a human subject, the method comprising administering to the subject a therapeutically effective amount of one or more C1 esterase inhibitors only at times of (i) the day of the transplantation but prior to reperfusion of the allograft kidney in the subject and (ii) about 24 hours after the transplantation,
   wherein the therapeutically effective amount of the one or more C1 esterase inhibitors combined, each time, is about 50 units/kg of the subject, wherein the therapeutically effective amount is effective for improving the estimated glomerular filtration rate (eGFR) at about one year post-transplantation to be higher than the subject's eGFR within one week following the transplantation and wherein the allograft kidney was obtained from an extended criteria donor (ECD) or from a donor after cardiac death (DCD).

2. The method of claim 1, wherein the one or more C1 esterase inhibitors are human plasma-derived C1 esterase inhibitors.

3. The method of claim 1, wherein the one or more C1 esterase inhibitors are administered intravenously.

4. The method of claim 3, wherein the kidney allograft function is improved for at least 12-15 months or more than 15 months after transplantation.

5. The method of claim 1, wherein improving the allograft kidney function further comprises one or more of decreased serum creatinine levels, increased creatinine clearance, and increased urine output.

6. The method of claim 1, wherein the kidney allograft is from a donor over the age of 60, or from a donor over the age of 50 with at least two of (i) a history of high blood pressure, (ii) a creatinine greater than or equal to 1.5 mg/dL, and (iii) death resulting from a stroke.

7. The method of claim 1, wherein the one or more C1 esterase inhibitors are administered subcutaneously.

* * * * *